United States Patent [19]

Vicik et al.

[11] Patent Number: 5,760,189

[45] Date of Patent: Jun. 2, 1998

[54] PROTEIN RECOVERY & PURIFICATION METHODS

[75] Inventors: Steven M. Vicik, Natick; Neil L. Schauer, Milford, both of Mass.; James R. Mercer, Derry, N.H.; Edward R. LaVallie, Tewksbury, Mass.; Catherine A. Briasco, Burlington, Mass.; Jeffrey S. Deetz, Melrose, Mass.; Dwight Winters, Camarillo, Calif.; Jenifer L. Thomas, Salem, N.H.

[73] Assignee: Genetics Institute, Inc., Cambridge, Mass.

[21] Appl. No.: 464,176

[22] Filed: Jun. 2, 1995

[51] Int. Cl.$^6$ .............................. C07K 1/14; C07K 1/18; C07K 1/32; C07K 1/36

[52] U.S. Cl. .................. 530/412; 530/416; 530/418; 530/422

[58] Field of Search ..................... 530/412, 416, 530/418, 422, 424

[56] References Cited

U.S. PATENT DOCUMENTS

| | | | |
|---|---|---|---|
| 4,988,798 | 1/1991 | Blum et al. | 530/399 |
| 5,128,150 | 7/1992 | Shanbron | 424/533 |
| 5,292,646 | 3/1994 | McCoy et al. | 435/69.7 |
| 5,451,662 | 9/1995 | Naveh et al. | 530/351 |
| 5,463,029 | 10/1995 | Dunn et al. | 530/416 |

FOREIGN PATENT DOCUMENTS

| | | |
|---|---|---|
| 0 499 541 A1 | 2/1992 | European Pat. Off. . |
| WO 82/02841 | 9/1982 | WIPO . |
| WO 91/07495 | 5/1991 | WIPO . |
| WO 94/02502 | 2/1994 | WIPO . |
| WO 94/05318 | 3/1994 | WIPO . |

OTHER PUBLICATIONS

Edwards, et al., J. Biol. Chem. 270(18):10764–10770 (1995).
LaVallie, et al., Biotechnology 11:187–193 (1993).
Williams, et al., Biochemistry 34:1787–1797 (1995).
Zaworski and Gill, Analytical Biochemistry 173(2):440–444 (1988).
Ames, J. of Bact. 160:1181–1183 (1984).
Aristidou et al., Biotechnology Letters 15:331–336 (1993).
Bardwell et al., Cell 67:581–589 (1991).
Belter et al., *Bioseparations—Downstream Processing for Biotechnology*: 77–94 (1988).
Bennett et al., Nature 334:268–270 (1988).
Bornstein and Balian, Cleavage at Asn–Gly bonds with hydroxylamine. *Meth. Enzymol.* 47(E):132–145 (1977).
Bradford, Analytical Biochemistry 72:248–254 (1976).
Bucke, *Prinicples of Biotechnology*, Wiseman eds.:151–171 (1983).
Dagert and Ehrlich,Gene 6:23–28 (1979).
De Smet et al., Biochim. Biophys. Acta 506:64–80 (1978).
Dunn and Studier, J. Mol. Biol. 166:477–535 (1983).
Edman et al., Nature 317:267–270 (1985).
Eklund et al., EMBO J. 3:1443–1449 (1984).
Ellis et al., Biochemistry 31:4882–91 (1992).
Englard et al., *Methods in Enzymology Volume 182*, Deutscher eds.:285–300 (1990).
Engler, *Protein Purification Process Engineering*, Harrison eds.:37–55 (1994).
Felix, Anal. Biochem. 120:211–234 (1982).
Hancock, Ann. Rev. Microbiol. 38:237–264 (1984).
Hettwer, Biotechnology and Bioengineering 33:886–895 (1989).
Holmgren, J. Biol. Chem. 264:13963–13966 (1989).
Ingram, J. Bacteriol. 146:331–336 (1981).
Kelley et al., Bioseparation 1:333–349 (1991).
Leipnieks et al., J. Biol. Chem. 254:1677–1683 (1979).
Leive, *Annals New York Academy of Sciences* 235:109–129 (1974).
Lim et al., J. Bacteriol., 163:311–316 (1985).
Maroux et al., J. Biol. Chem. 246:5031–5039 (1971).
Mazzarella et al., J. Biol. Chem. 265:1094–1101 (1990).
Moir et al., *Separation Processes in Biotechnology*, Asenjo eds.: 67–94 (1990).
Naglak et al., *Separation Processes in Biotechnology*, Asenjo eds.:177–205 (1990).
Norrander et al., Gene 26:101–106 (1983).
Nossal et al., J. Biol. Chem. 241:3055–3062 (1966).
Paul et al., Proc. Natl. Acad. Sci. U.S.A. 87:7512–7516 (1990).
Pennell, *The Plasma Proteins Volume 1*, Putnam eds.:9–42 (1960).
Sanger et al., J. Mol. Biol. 162:729–773 (1982).
Sassenfeld, TIBTECH 8:88–93 (1990).
Scawen et al., *Handbook of Enzyme Biotechnology 2nd edition*, Wiseman eds.:15–53 (1985).
Schagger, et al., Anal Biochem. 166:368–379 (1987).
Scopes, *Protein Purification Principles and Practice 2nd edition*, Cantor eds. 21–71 (1987).
Scopes, *Protein Purification Principles and Practice 3rd edition*, Cantor eds. 22–43;171 (1994).
Spears, *Biotechnology vol 3–Bioprocessing*, Rehm eds:40–55 (1993).
Strandberg et al., Process Biochemistry 26:225–234 (1991).
Takagi et al., Nucl. Acids Res. 13:2063–2074 (1985).
Vaara, Microbiological Reviews 56:395–411 (1992).
Wang et al., eds, *Fermentation and Enzyme Technology*:253–256 (1979).
Wheelwright, *Protein Purification: Design and Scale up of Downstream Processing*: 87–98 (1991).
Windholtz et al., *The Merck Index 10th Edition*: 300 & 1364 (1983).
Xia, Protein Science I:310–321 (1992).

*Primary Examiner*—Stephen Walsh
*Assistant Examiner*—Darryl A. Basham
*Attorney, Agent, or Firm*—M. C. Meinert; Thomas J. DesRosier

[57] ABSTRACT

Provided by the present invention are novel methods of protein recovery and purification methods and more specifically novel methods for the recovery and purification thioredoxin fusion proteins, especially of IL-11.

103 Claims, No Drawings

PROTEIN RECOVERY & PURIFICATION METHODS

FIELD OF INVENTION

The present invention relates generally to novel protein recovery and purification methods and more specifically to novel methods for the recovery and purification of thioredoxin-like fusion proteins, especially of IL-11.

BACKGROUND OF THE INVENTION

The advent of recombinant technology now allows for the production of high levels of proteins within suitably transformed host cells. Where the host cell does not secrete the protein of interest, it is necessary to release the protein from the cells and to then further purify the protein.

The initial step in the purification of an intracellular protein is release of the protein to the extracellular medium. This is typically accomplished using mechanical disruption techniques such as homogenization or head milling. While the protein of interest is generally effectively liberated, such techniques have several disadvantages. Engler, *Protein Purification Process Engineering*, Harrison eds. :37–55 (1994). Temperature increases, which often occur during processing, may result in inactivation of the protein. Moreover, the resulting suspension contains a broad spectrum of contaminating proteins, nucleic acids, and polysaccharides. Nucleic acids and polysaccharides increase solution viscosity, potentially complicating subsequent processing by centrifugation, cross-flow filtration, or chromatography. Complex associations of these contaminants with the protein of interest can complicate the purification process and result in unacceptably low yields. As such, more selective means of releasing intracellular proteins facilitates further downstream processing. Several techniques have been reported to permeabilize cells and/or to extract intracellular proteins. These methods include the use of solvents, detergents, chaotropic agents, antibiotics, enzymes, and chelating agents to enhance cell permeability and/or promote extraction. Additions of certain compounds, such as glycine, to the fermentation medium during culture growth have also been reported to promote release of certain intracellular enzymes. Finally, techniques such as freeze-thaw treatment or osmotic shock have also been shown to release subsets of intracellular proteins.

However, these techniques are not necessarily applicable to all intracellular *E. Coli* proteins, and all have limited application for large scale processing, and/or other disadvantages.

For example, while solvents such as toluene and chloroform promote release of intracellular proteins, these substances are known to be toxic and/or carcinogenic. Belter et al., *Bioseparations—Downstream Processing for Biotechnology*:77–94 (1988). Ames, J. of Bact. 160:1181–1183 (1984). Windholtz et al., *The Merck Index 10th Edition*: 300 & 1364 (1983). Naglak et al., *Separation Processes in Biotechnology*, Asenjo eds.:177–205 (1990). ionic detergents, such as SDS, often irreversibly denature isolated proteins (Scopes, *Protein Purification Principles and Practice 3rd edition*, Cantor eds., 22–43 (1994)). Although non-ionic detergents like Triton X-1100 or Triton X-114 are not normally denaturating, the recovered proteins are often associated with detergent micelles which can require additional processing to yield detergent-free protein. Scopes, supra. Chaotropic agents, such as urea and guanidine hydrochloride, can be denaturing at the concentrations required for complete release (Naglak et al., supra. Hettwer, Biotechnology and Bioengineering 33:886–895 (1989)). Their effectiveness may be dependent on the growth phase of the culture (Ingram, L., Bacteriol. 146:331–336 (1981)). Antibiotics, such as polymyxin B, which affect the permeability of *E. coli* (Hancock, Ann. Rev. Microbiol. 38:237–264 (1984)), are not typically used in the pharmaceutical industry due to general concerns over the use of antibiotics in manufacturing processes. The use of lysozyine, which provides for a relatively gentle means of protein release, is limited because of its relatively high cost of the enzyme (Belter et al., supra., Naglak et al., supra.) and because of the subsequent need to purify the protein of interest from the enzyme reagent (Naglak et al., supra.). In addition, chelating agents, often used to enhance the effectiveness of other permeabilizing/release techniques such as lysozyme (Naglak et al., supra, Bucke, *Principles of Biotechnology*, Wiseman eds.: 151–171 (1983)), toluene (De Smet et al., Biochim. Biophys. Acta 506:64–80 (1978)), or Triton X-100 (Leive, *Annals New York Academy of Sciences* 235:109–129 (1974)) extraction, suffer from the disadvantage of non-specific release of the protein of the protein of interest. For example, the use of chelator releases up to 18% of intracellular *E. coli* protein and can result in undesired complex formation with lipopolysaccharidies (LPS) and phosphatidyl-ethanolamine. Naglak, et al. supra at 185.

The use of other methods for protein release also have disadvantages. For example, osmotic shock, in which cells are suspended in a high osmolarity medium, recovered, and subsequently placed in a low osmolarity buffer (Nossal et al., J. Biol. Chem. 241:3055–3062 (1966)) requires additional processing steps with respect to other extraction alternatives (Moir et al. *Separation Processes in Biotechnology*, Asenjo eds: 67–94 (1990)) or necessitates the handling of large liquid volumes at low temperatures (Naglak et al., supra.). This renders the method unattractive for large scale processing. Freeze-thaw treatment also releases intracellular proteins, although relatively low yields often result in multiple cycles or additional processing requirements (Naglak et al., supra.; Bucke, supra.). In addition, cell paste freezing is an added non-trivial processing requirement compared with other extraction alternatives. Finally, reagents, such as glycine, have been added during fermentation to promote protein release to the extracellular medium (Aristidou et al., Biotechnology Letters 15:331–336 (1993)). While partial release of several intracellular proteins has been reported, this approach requires direct coupling of fermentation and release strategies and subsequent separation of the protein of interest from a potentially complex extracellular broth.

Once the protein is released from the host cell, purification of the protein of interest from other cell components is required. Unfortunately, most extraction approaches, such as cell lysis, not only expose the protein to potential degradation by host cell proteases, but also, make isolation of the protein from other elements of the resulting suspension more difficult. For example, the presence of negatively charged molecules, such as DNA, RNA, phospholipids, and lipopolysaccharides (LPS), often require the use of anion exchange chromatography (Sassenfeld, TIBTECH 8:88–93 (1990).; Spears, *Biotechnology* vol 3— *Bioprocessing*, Rehm eds:40–51 (1993)) and/or precipitation with polycations, such as protamine sulfate (Kelley et al., Bioseparation 1:333–349 (1991); Scopes, *Protein Purification Principles and Practice*, 2nd *edition*, Cantor eds., 21–71 (1987)), streptomycin sulfate (Wang et al. eds, *Fermentation and Enzyme Technology*:253–256 (1979)), polyethylenimine (PEI) (Kelley et al., supra.; Sassenfeld, supra.), and/or aqueous two phase extraction with immiscible polymer systems such as polyethylene glycol (PEG)/phosphate or PEG/dextran (Kelley et al., supra., Strandberg et al., Process Biochemistry 26:225–234 (1991).). Alternatively, the protein of interest may be precipitated away from non-proteinaceous polyanionic contaminants through the addition of a neutral salt such as ammonium sulfate or potassium chloride (Wheelwright, *Protein Purification: Design and Scale up of Downstream Processing:* 87–98 (1991); Englard et al., *Methods in Enzymology* Volume 182, Deutscher eds.: 285–300 (1990)) and/or a polymer such as PEG or dextran sulfate (Wang et al., supra.; Wheelwright, supra.). Where the protein of interest is positively charged, it will tend to bind to any negatively charged molecules present thereby making purification of the protein virtually impossible.

Typically, researchers have utilized the initial fractionation steps, described above, to separate the offending polyanions from the protein of interest. Unfortunately, each of these initial separation methods suffers from severe disadvantages, especially when used in the manufacture of pharmaceutical reagents. For example, the large quantities of non-proteinaceous polyanionic contaminants found in bacterial lysates tend to reduce the binding capacities of anion exchange chromatography resins. In addition, regeneration protocols are often rendered ineffective due to tenacious binding of the polyanions to the resins (Spears, supra.). Finally, the low ionic strength conditions that favor protein binding are ineffective at disrupting polyanion-protein interactions and result in a lack of separation (Scopes, *Protein Purification Principles and Practice* 3rd edition, Cantor eds. 171 (1994)). Protamine sulfate preparations are plagued by concerns over protease and viral contaminations. Moreover, unwanted protein precipitation can occur using this reagent (Scopes, *Protein Purification Principles and Practice* 2nd edition, Cantor eds., 21–71 (1987)). In the processing of pharmaceutical proteins, streptomycin sulfate is generally not used due to general apprehension over the use of antibiotics as process reagents (Scawen et al., *Handbook of Enzyme Biotechnology* 2nd edition, Wiseman eds.: 15–53 (1985)). PEI preparations are often contaminated with varying amounts of the ethylenimine monomer, a suspected cancer agent (Scawen et al., supra.). PEI also tends to bind irreversibly to many chromatography resins, thereby limiting their effectiveness and the number of potential chromatography resins available for use post-PEI clarification. In general, aqueous two phase extractions systems are difficult to predict and often require an empirical approach for determining conditions that move the protein of interest into the appropriate aqueous phase (Kelley et al., supra.). Techniques that specifically precipitate the protein of interest often result in the entrapment of the non-proteinaceous contaminants in the precipitate rendering the separation ineffective (Scopes, supra.; Wheelwright, *Protein Purification: Design and Scale up of Downstream Processing:* 87–98 (1991)).

Accordingly, there continues to exist a need in the art for both effective protein release methods (that minimize or eliminate release of non-proteinaceous contaminants) as well as effective purification methods (that remove non-proteinaceous contaminants, especially polyanionic contaminants) and an overall release and purification process that is readily executed at large scale.

BRIEF SUMMARY OF THE INVENTION

Provided by the present invention is a method for the release and purification of a thioredoxin-like fusion protein from the cell into a solution by adding chelator to the solution which releases the fusion protein from the cell. Optionally, the temperature prior to the addition of chelator may be substantially cooler than after the addition of chelator, e.g., representing a 20–40 degree C temperature differential, with a 35° C. differential preferred. The method is particularly amenable to large scale processing, as defined to be greater than 10 L of cell suspension volume, and upwards of hundreds of liters of total volume. Divalent cation/alcohol solution is then added thereby forming a soluble fraction, which contains the fusion protein, and an insoluble fraction, which contains unwanted contaminants. The divalent cation includes for example magnesium, manganese and calcium, alone or in combination. The alcohol can be methanol, ethanol, propanol, isopropanol, isobutanol, and tertiary-butanol. Preferably, the final alcohol concentration is from 5 to 30% with 14% ethanol being preferred. The resulting divalent cation concentration can range from 1 to 1000 mM, with preferred being 50 to 200 mM, and most preferred being 200 mM magnesium. Also preferred are a combination of 125 mM magnesium and 75 mM calcium; 125 mM magnesium and 75 mM manganese; as well as 125 mM magnesium, 38 mM manganese and 38 mM calcium.

In another embodiment of the present invention, zinc can be added to the first soluble fraction obtained above, thereby forming a second insoluble fraction from which the fusion protein can be isolated. Optionally, chelator can be added to solubilize the protein from the second insoluble fraction. Suitable sources of zinc include zinc chloride, zinc sulfate, and zinc acetate. The final zinc concentration can be from 1 to 500 mM, with 50 mM zinc chloride being preferred.

Protein of the present invention can be either recombinantly produced in a transformed host cell, e.g., *E. coli*, and purified from the host cell or can be purified from soluble sources such as plasma, urine, and the like. When purifying from soluble sources, the initial release step utilizing chelator can be omitted and the purification can begin immediately with the addition of the divalent cation/alcohol solution as described above.

Specifically provided by the present invention is a method for release of a thioredoxin-IL-11 fusion protein from a cell into a solution by adding EDTA, followed by adding stock solutions of $MgCl_2$, ethanol, and $CaCl_2$ resulting in a solution comprised of 125 mM magnesium chloride, 75 mM calcium chloride, and 14% ethanol, and isolating the fusion protein from the soluble fraction formed. The final concentration of EDTA can range from 0.1 to 100 mM, with 15 mM being preferred. In a presently preferred embodiment, the temperature prior to the addition of the chelator is substantially cooler than after the addition of chelator, for example going from about 3° C. to about 37° C. The resulting concentration of magnesium chloride and calcium chloride can range from 1 to 1000 mM and the final ethanol concentration can range from 5 to 30%.

In another embodiment of the present invention, the protein of interest can be purified by taking advantage of a difference in pI of the protein of interest, as compared to the pI of the fusion protein and the fusion partner. Prior to cleavage of the fusion protein, two complementary ion exchange resins are utilized back to back and after cleavage of the fusion protein, two additional complementary ion exchange resins are utilized back to back. The purification process takes advantage of the fact that the pI of the fusion protein, i.e., the fusion partner linked to the protein of interest, is not the same as the pI of the protein of interest sans the fusion partner.

According to the present invention, an adsorptive step is coupled with a non-adsorptive step to rigorously remove oppositely charged molecules under the conditions employed and to enhance the effectiveness and selectivity imparted by the cleavage reaction. This entails both selection of appropriate resins and the corresponding optimization of pH and ionic strength conditions to leverage the pI differential of fusion proteins from the protein of interest and the fusion partner. To purify the fusion protein it is desirable to have the pH as close to the pI so as to exclude oppositely charged contaminants; after cleavage it is desirable to have the pH as close to the pI of the protein of interest to exclude all oppositely charged contaminants. Typically, adjusting the pH only in the chromatography steps does not provide the requisite level of contaminant removal. Accordingly, the invention provides for the addition of non-adsorptive steps as "ionic filters" to obtain the requisite log removals of contaminants. The particular combinations of complementary ion exchange resins chosen provides much greater levels of purification than is possible with traditional ion exchange methodology.

According to the method of invention, the thioredoxin-like fusion protein is bound to a first resin, eluted, applied to a second resin (to which it does not bind) and is collected in the unbound fraction; next, the thioredoxin fusion protein is cleaved and the cleaved protein is bound to a third resin, eluted, applied to a fourth resin and collected in the unbound fraction from the fourth resin. Where the first and fourth resins are anion exchange resins, the second and third resins are cation exchange resins. Where the first and fourth resins are cation exchange resins, the second and third resins are anion exchange resins. The resins are selected based upon the pI of the fusion protein and the pI of the protein of interest. For example, where the fusion protein is negatively charged prior to cleavage, and the protein of interest is positively charged after cleavage, the first and fourth resins are anion exchange resins, and the second and third resins are cation exchange resins. Alternatively, where the fusion protein is positively charged prior to cleavage, and the protein of interest is negatively charged after cleavage, the first and fourth resins are cation exchange resins, and the second and third resins are anion exchange resins. Suitable anion exchange resins have positively charged groups such as diethyleaminoethane (DEAE), polyethyleneimine (PEI), and quaternary aminoethane (QAE). Suitable cation exchange resins have negatively charged groups such as sulfonyl, sulfylpropyl (SP), carboxyl, and carboxy methyl.

Also provided by the present invention is a method for purifying IL-11 which involves binding thioredoxin-IL-11 to a first anion exchange resin, such as Toyopearl QAE, eluting with a first eluant (where the preferred eluants include 20–100 mM Tris buffers at pH 7.5–8.5, containing 100–500 mM NaCl, and 50–200 mM Histidine buffers at pH 5.5–6.6,containing 0–150 mM NaCl, with the most preferred eluant being 75 mM Histidine, 75 mM NaCl, at pH 6.2), applying this eluate to a first cation exchange resin, such as S Sepharose Fast Flow, collecting the thioredoxin-IL-11 in an unbound fraction, then cleaving the thioredoxin-IL-11 fusion protein to form positively charged IL-11, binding to a second cation exchange resin such as CM Sepharose Fast Flow (where the preferred eluants include 50–300 mM glycine buffers at pH 9.0–10.0, containing 100–500 mM NaCl, with the most preferred eluant being 150 mM glycine, 150 mM NaCl, pH 9.5), applying this second eluate to a second anion exchange resin such as Toyopearl QAE, and then collecting the IL-11 in the unbound fraction.

DETAILED DESCRIPTION OF THE INVENTION

For the large-scale production of a protein which has been recombinantly produced, protein is typically first released from the cell. Proteins can be produced as a fusion protein, for example as a thioredoxin fusion in *E. coli* , and are thought to be directed towards sites at which the inner and outer cell membranes become contiguous, sometimes referred to as Bayer's patches, through the influence of the thioredoxin fusion partner. According to the method of the present invention, host cells are selectively permeabilized, using a chelator such as Tris-EDTA, to release the fusion protein of interest. Chelators other than EDTA can also be used, for example, DPTA, EGTA, CDTA, citrate, and the like. The process is readily optimized for the concentration range of the chelator, the temperature of the reaction, as well as the pH and ionic strength of the solution, as is well within the skill of one skilled in the art. As one skilled in the art readily appreciates, the appropriate concentration of chelator will vary according to the nature of the solute, solution pH, solution temperature, solution ionic strength, and the molar proportion of chelator to metal chelate. Preferred are aqueous solutions of a pH between 2 and 11, a temperature between 10° C. and 60° C., the ionic strength between 0 and 1, and the molar ratio of chelator to chelate ranging from 0.1:1.0 to 1.0:0.1. Optimal conditions can be readily ascertained by one skilled in the art by monitoring the release of the protein of interest from the host cells. Typically, final chelator concentrations range from 0.1 mM to 100 mM, with 15 mM preferred. In a presently preferred embodiment, the temperature prior to the addition of the chelator is substantially cooler than after the addition of chelator, for example going from about 3° C. to about 37° C.

Lipopolysaccharides in the outer membrane of gram negative bacteria form ionic interactions with magnesium and/or calcium ions (Vaara, Microbiological Reviews 56:395–411 (1992); Hancock, Ann. Rev. Microbiol. 38:237–264 (1984); Felix, Anal. Biochem. 120:211–234 (1982). Presumably, the chelator acts on divalent ions, e.g., magnesium and calcium ions, as a counter-ion to negatively charged groups. This leads to a dissociation, which in turn, leads to the generation of gaps in the membrane allowing for the selective release of the fusion protein.

After release of the fusion protein into the medium, the cellular debris can be removed if desired, for example, by centrifugation. However, one of the advantages of the present invention is that it does not require removal of cellular debris, as is usually required with other clarification methods. Present in solution are negatively charged molecules such as DNA, RNA, phospholipids and lipopolysaccharides, as well as the fusion protein of interest. Where the fusion protein of interest is positively charged, it will bind to any negatively charged molecules making purification of the protein virtually impossible. Well known to those skilled in the art is the use of polyethylenimine (PEI) for the removal of DNA (Scawen, et al., supra). Unfortunately, PEI is always contaminated with residual amounts of the monomer, ethylenimine (EI) (Scawen et al., supra.), which has been classified by OSHA to be a cancer-suspect agent. According to the present invention, the removal of the negatively charged molecules from solution can be accomplished utilizing a mixture of one or more divalent cations, such as magnesium, manganese, and/or calcium plus alcohol, e.g., $Mg^{++}/ROH$, where R is a short carbon chain, 1 to 4 carbons in length, such as methyl, ethyl and the various isomers of propyl, as well as secondary butyl and tertiary butyl, with ethyl being preferred. Divalent cations are typically added as salts with counteranions such as chloride, sulphate, acetate, and the like. This divalent cation/alcohol solution is sometimes referred to herein simply as the "alcohol solution."

Upon addition of the alcohol solution, most, if not all of the protein of interest remains in solution, whereas the contaminants precipitate out of solution forming an insoluble fraction. This step is also concentration, pH, temperature, and time-dependent. Prolonged incubation under optimum conditions may result in irreversible precipitation of the protein of interest. Elevated temperatures, and/or alcohol concentrations, and/or pH extremes may increase precipitation of protein. Temperatures lower than 50° C. and final alcohol concentrations between 5 and 30% are preferred, with 32° C. and 14% (volume/volume %) ethanol most preferred. Insufficient divalent cation and/or alcohol concentrations lead to ineffective clarification removal of non-proteinaceous contaminants). Preferably, the final divalent cation concentration is 1 to 1000 mM; or 50 to 300 mM, with the most preferred range being 50 to 200 mM.

Optionally, for increased clarification, manganese and/or calcium salts can be added to the $Mg^{++}$/ROH solution, at a final concentration of 1 to 1000 mM, so that the total molarity remains in the range of 1 to 1000 mM, or 50 to 300 mM, with the most preferred range currently contemplated being 50 to 200 mM. When multiple divalent cations are utilized, preferred final concentrations total 50 to 200 mM salt and include, for example, 125 mM magnesium plus 75 mM calcium or manganese, or various combinations thereof, for example, about 125 mM magnesium, plus about 38 mM manganese and about 38 mM calcium. As used herein, the term "molarity" means the number of gram molecular weights of a compound dissolved in one liter of solution.

Addition of the alcohol solution removes greater than 80–90% of the DNA and LPS molecules from solution. The resulting solution can then be further treated to remove the protein of interest from solution. For example, the protein of interest can be precipitated using zinc ($Zn^{++}$) salts such as zinc chloride, zinc sulphate, zinc acetate and the like. The resulting precipitate can be concentrated and recovered by solid/liquid separation techniques including centrifugation and filtration. Precipitated protein can be subsequently solubilized by a chelating agent such as EDTA, DPTA, EGTA, CDTA, or citrate and further purified. Optionally, the precipitate may he stored prior to solubilization. The process can be optimized for zinc concentration, chelator to metal concentration, pH, temperature, and time, as is readily appreciated by one skilled in the art and can be readily adjusted for the protein of interest. As is known in the art, irreversible protein precipitation may occur in the presence of organic solvents, such as methanol, ethanol, and acetone (Pennell, *The Plasma Proteins Volume* 1, Putnam eds.:9–42 (1960); Wang et al. eds, *Fermentation and Enzyme Technology*:253–256 (1979).; Wheelwright, *Protein Purification: Design and Scale up of Downstream Processing:* 87–98 (1991).; Scopes, *Protein Purification Principles and Practice* 2nd edition, Cantor eds., 21–71 (1987)). This phenomenon is typically minimized by operating at lower temperatures for shorter durations. Preferred conditions for precipitation of the protein of interest are generally pH=6.0 to 8.5, 1 to 500 mM $Zn^{++}$, a temperature lower than 20° C., and duration of fewer than 24 hours. Most preferred conditions are precipitation at pH=7.0 and 0° C. for 15 minutes at a final $ZnCl_2$ concentration of 50 mM.

Subsequently, the precipitate is recovered by solid/liquid separation methods known in the art which may then be efficiently stored. At this stage of processing, the protein is no longer in solution and it is less susceptible to proteolysis. In addition, the protein is concentrated at least an order of magnitude, which readily allows for long term (circa 2 months) frozen storage at −20° C. to −80° C. of large scale process intermediates. Accordingly, this step is for de-coupling recovery from purification portions of the process.

Prior to further processing, the protein precipitate is solubilized with a chelating agent. Preferred solubilization conditions are pH=6.5 to 11,temperature lower than 40° C., and a ratio of moles of chelator per moles $Zn^{++}$ of about 0.5 to 1000. Most preferred is solubilization at pH=8.0 and 20° C. using the chelator EDTA at a ratio of 5–100 moles EDTA per mole $Zn^{++}$. Typically, greater than 70% of the protein of interest is recovered through precipitation, solid liquid separation, and solubilization processing.

Alternatively, or in addition, the fusion protein of interest can be further purified. Purification can be accomplished using two ion exchange resins prior to cleavage of the fusion protein, followed by two ion exchange resins after cleavage of the fusion protein. The process leverages any difference in the pI of the fusion protein, i.e., the fusion partner linked to the protein of interest, from the pI of the protein of interest sans fusion partner. For example, where the protein of interest has been expressed as a fusion partner, and where the fused form of the protein has a pI that is substantially different from the pI of the cleaved form (for example, where the fused form of the protein has a basic pI, and where the cleaved form has an acidic pI; or vice versa, the fused form being acidic and the cleaved form being basic), it is possible to advantageously utilize this difference in pI for purification of the cleaved form using complementary ion exchange resins.

More specifically, the fusion protein is first purified with the appropriate type of ion exchange resin: for example, an anion-exchange resin to bind a negatively charged fusion protein, (or conversely, a cation-exchange resin to bind a positively charged fusion protein). Next, the complementary type of ion exchange resin is used to further remove contaminants from the process stream having a pI and net charge at the pH of operation that is different from the fused form of the protein. For example, in the case of a fusion protein with an acidic pI, a cation exchange resin can be used under conditions i.e., where the pH is greater than the pI of the fusion protein in which the fusion protein flows through the resin without binding, while the resin binds contaminants with pIs greater than the pH of operation (or, conversely, in the case of a fusion protein with a basic pI, an anion exchange resin can be used under conditions i.e., where the pH is less than the pI of the fusion in which the fusion protein flows through the resin without binding, while the resin binds contaminants with pIs less than the pH of operation). The pH requirements may be modified by the addition of compounds that alter the ionic strength of the solution as is understood by one skilled in the art of ion exchange chromatography. The fusion protein is simply collected in the unbound fraction, also sometimes referred to as the flow through fraction. It is these complementary combinations of ion-exchange purifications that result in a preparation of fusion protein that has been purified away from contaminants with markedly different pIs.

Next, the fusion protein can he cleaved into the constituent proteins, namely the protein of interest having a significantly different pI from the fused form, and the fusion partner. Purification of the protein of interest can then proceed with additional applications of ion-exchange chromatography. Where once the fused form did bind to the resin, the cleaved protein of interest now flows through the resin without binding, while contaminants, (including uncleaved fusion protein and/or the fusion partner which is that part of the protein of interest released during cleavage)

do bind to the resin (or, conversely, where once the fused form flowed through the resin without binding, the cleaved protein of interest now binds to the resin while contaminants do not). More specifically, the products of the cleavage reaction are first applied, for example, to a cation exchange resin (where the cleaved protein is positively charged, or conversely, to an anion exchange resin if the product protein is negatively charged). Next, the complementary ion exchange resin, for example, an anion exchange resin (or conversely, a cation exchange resin) is used under conditions where the cleaved protein flows through the resin without binding, while the negatively charged contaminants (conversely, positively charged contaminants) do bind to the resin. The protein of interest is collected in the flow through. Again, these additional ion exchange combinations further purify away contaminants having pIs markedly different from the protein of interest.

Many combinations of complementary ion exchange resins are possible. Set forth in Table 1, below are eight variations, four for the case of a negatively charged fusion protein with a positively charged cleaved protein) and four for the case of a positively charged fusion protein (with a negatively charged cleaved protein).

TABLE 1

COMPLEMENTARY ION EXCHANGE COMBINATIONS

Negatively charged fusion protein
Positively charged cleaved protein

| I | II | III | IV |
|---|---|---|---|
| Anion exchange (bind) ↓ | Cation exchange (no bind) ↓ | Cation exchange (no bind) ↓ | Anion exchange (bind) ↓ |
| Cation exchange (no bind) ↓ | Anion exchange (bind) ↓ | Anion exchange (bind) ↓ | Cation exchange (no bind) ↓ |
| Cleave ↓ | Cleave ↓ | Cleave ↓ | Cleave ↓ |
| Cation exchange (bind) ↓ | Cation exchange (bind) ↓ | Anion exchange (no bind) ↓ | Anion exchange (no bind) ↓ |
| Anion exchange (no bind) | Anion exchange (no bind) | Cation exchange (bind) | Cation exchange (bind) |

Positively charged fusion protein
Negatively charged cleaved protein

| V | VI | VII | VIII |
|---|---|---|---|
| Cation exchange (bind) ↓ | Anion exchange (no bind) ↓ | Anion exchange (no bind) ↓ | Cation exchange (bind) ↓ |
| Anion exchange (no bind) ↓ | Cation exchange (bind) ↓ | Cation exchange (bind) ↓ | Anion exchange (no bind) ↓ |
| Cleave ↓ | Cleave ↓ | Cleave ↓ | Cleave ↓ |
| Anion exchange (bind) ↓ | Anion exchange (bind) ↓ | Cation exchange (no bind) ↓ | Cation exchange (no bind) ↓ |
| Cation exchange (no bind) | Cation exchange (no bind) | Anion exchange (bind) | Anion exchange (bind) |

The particular variation chosen depends upon which configuration of complementary exchange resins provides the greatest efficiency of purification. For example, for the purification of thioredoxin-IL-11, surprisingly it has been found that the first configuration (I) gives the most efficient purification. Certain positively charged contaminants unexpectedly bind to the first anion exchange resin and are eluted along with the thioredoxin-IL-11 fusion protein. These positively charged contaminants then bind to the following cation exchange resin while the thioredoxin-IL-11 fusion protein does not and simply flows through. Thus, for certain applications, it may be preferable to select a pre-cleavage configuration in which the fusion protein is bound in the first step, thereby allowing most of the contaminants to remain in the flow-through fraction. Similarly, it may be preferable to select a post-cleavage configuration in which the cleaved protein of interest is bound in the first post-cleavage step, thereby allowing the majority of contaminants to remain in the flow-through fraction.

Suitable eluants to elute the protein of interest from the anion exchange resin are well known to one skilled in the art and include, for example, any buffered solution capable of maintaining pH at the desired value and also containing from 0 to 1.0M of an ionic salt capable of causing desorption of the protein from the resin.

Suitable eluants to elute the protein of interest from the cation exchange resin are well known to one skilled in the art and include, for example, any buffered solution capable of maintaining pH at the desired value and also containing from 0 to 1.0M of an ionic salt capable of causing desorption of the protein from the resin.

According to the present invention, the DNA sequence encoding a heterologous peptide or protein selected for expression in a recombinant system is desirably fused to a thioredoxin-like DNA sequence for expression in the host cell. A thioredoxin-like DNA sequence is defined herein as a DNA sequence encoding a protein or fragment of a protein characterized by an amino acid sequence having at least 30% homology with the amino acid sequence of *E. coli* thioredoxin. Incorporated by reference is McCoy, et al., U.S. Pat. No. 5,292,646; issued Mar. 8, 1994 which discloses an *E. coli* thioredoxin sequence (SEQ ID NO. 22,therein). Alternatively, a thioredoxin-like DNA sequence is defined herein as a DNA sequence encoding a protein or fragment of a protein characterized by having a three dimensional structure substantially similar to that of human or *E. coli* thioredoxin and optionally by containing an active-site loop. The DNA sequence of glutaredoxin is an example of a thioredoxin-like DNA sequence which encodes a protein that exhibits such substantial similarity in three-dimensional conformation and contains a Cys . . . Cys active site loop. The amino acid sequence of *E. coli* thioredoxin is described in H. Eklund et al., EMBO J. 3:1443–1449 (1984). The three-dimensional structure of *E. coli* thioredoxin is depicted in FIG. 2 of A. Holmgren, J. Biol. Chem. 264:13963–13966 (1989). In FIG. I of McCoy, et al., supra, nucleotides 2242–2568 encompasses a DNA sequence encoding the *E. coli* thioredoxin protein (Lim et al., J. Bacteriol., 163:311–316 (1985)) (McCoy, et ail., supra). A comparison of the three dimensional structures of *E. coli* thioredoxin and glutaredoxin is published in Xia, Protein Science 1:310–321 (1992). These four publications are incorporated herein by reference for the purpose of providing information on thioredoxin-like proteins that is known to one of skill in the art.

As the primary example of a thioredoxin-like protein useful in this invention, *E. coli* thioredoxin has the following characteristics. *E. coli* thioredoxin is a small protein, only 11.7 kD, and can be produced to high levels (>10%, corresponding to a concentration of 15 μM if cells are lysed at 10 $A_{550}$/ml). The small size and capacity for a high level synthesis of the protein contributes to a high intracellular concentration. *E. coli* thioredoxin is further characterized by a very stable, tight structure which can minimize the effects on overall structural stability caused by fusion to the desired peptide or proteins.

The three dimensional structure of *E. coli* thioredoxin is known and contains several surface loops, including a distinctive Cys . . . Cys active-site loop between residues $Cys_{33}$ and $Cys_{36}$ which protrudes from the body of the protein. This Cys . . . Cys active-site loop is an identifiable, accessible surface loop region and is not involved in any interactions with the rest of the protein that contribute to overall structural stability. It is therefore a good candidate as a site for peptide insertions. Both the amino- and carboxyl-termini of *E. coli* thioredoxin are on the surface of the protein, and are readily accessible for fusions. Human thioredoxin, glutaredoxin and other thioredoxin-like molecules also contain this Cys. . . Cys active-site loop.

*E. coli* thioredoxin is also stable to proteases. Thus, *E. coli* thioredoxin may be desirable for use in *E. coli* expression systems, because as an *E. coli* protein it is characterized by stability to *E. coli* proteases. *E. coli* thioredoxin is also stable to heat up to 80° C. and to low pH.

Other thioredoxin-like proteins encoded by thioredoxin-like DNA sequences useful in this invention share homologous amino acid sequences, and similar physical and structural characteristics. Thus, DNA sequences encoding other thioredoxin-like proteins may be used in place of *E. coli* thioredoxin according to this invention. For example, the DNA sequence encoding other species' thioredoxin, e.g., human thioredoxin, have been employed by these inventors in the compositions and methods of this invention. Human thioredoxin has a three-dimensional structure that is virtually superimposable on *E. coli*'s three-dimensional structure, as determined by comparing the NMR structures of the two molecules. Human thioredoxin also contains an active-site loop structurally and functionally equivalent to the Cys . . . Cys active-site loop found in the *E. coli* protein. Human IL-11 fused in frame to the carboxyl terminus of human thioredoxin (i.e., a human thioredoxin/IL-11 fusion) exhibited the same expression characteristics as the *E. coli* thioredoxin/IL-11 fusion exemplified in Examples 1–2. Consequently, human thioredoxin is a thioredoxin-like molecule and can be used in place of or in addition to *E. coli* thioredoxin in the production of protein and small peptides in accordance with the method of this invention. Insertions into the human thioredoxin active-site loop and onto the amino terminus may be as well tolerated as those in *E. coli* thioredoxin.

Other thioredoxin-like sequences which may be employed in this invention include all or portions of the protein glutaredoxin and various species' homologs thereof. (A. Holmgren, cited above.) Although *E. coli* glutaredoxin and *E. coli* thioredoxin share less than 20% amino acid homology, the two proteins do have conformational and functional similarities (Eklund et al., EMBO J. 3:1443–1449 (1984)) and glutaredoxin contains an active-site loop structurally and functionally equivalent to the Cys . . . Cys active-site loop of *E. coli* thioredoxin. Glutaredoxin is therefore a thioredoxin-like molecule as herein defined.

The DNA sequence encoding protein disulfide isomerase (PDI), or that portion thereof containing the thioredoxin-like domain, and its various species' homologs (Edman et al., Nature 317:267–270 (1985)) may also be employed as a thioredoxin-like DNA sequence, since a repeated domain of PDI shares >30% homology with *E. coli* thioredoxin and that repeated domain contains an active-site loop structurally and functionally equivalent to the Cys . . . Cys active-site loop of *E. coli* thioredoxin. These three publications are incorporated herein by reference for the purpose of providing information on glutaredoxin and PDI which is known and available to one of skill in the art.

Similarly the DNA sequence encoding phosphoinositide-specific phospholipase C (PI-PLC), fragments thereof and various species' homologs thereof (Bennett et al., Nature 334:268–270 (1988)) may also be employed in the present invention as a thioredoxin-like sequence based on their amino acid sequence homology with *E. coli* thioredoxin, or alternatively based on similarity in three-dimensional conformation and the presence of an active-site loop structurally and functionally equivalent to the Cys . . .Cys active-site loop of *E. coli* thioredoxin. All or a portion of the DNA sequence encoding an encloplasmic reticulum protein, such as ERp72,or various species homologs thereof are also included as thioredoxin-like DNA sequences for the purposes of this invention (Mazzarella et al., J. Biol. Chem. 265:1094–1101 (1990)) based on amino acid sequence homology, or alternatively based on similarity in three-dimensional conformation and the presence of an active-site loop structurally and functionally equivalent to the Cys . . . Cys active-site loop of *E. coli* thioredoxin. Another thioredoxin-like sequence is a DNA sequence which encodes all or a portion of an adult T-cell leukemia-derived factor (ADF) or other species homologs thereof. N. Wakasugi et al., Proc. Natl. Acad. Sci. U.S.A 87:8282–8286 (1990). ADF is now believed to be human thioredoxin. Similarly, the protein responsible for promoting disulfide bond formation in the periplasm of *E. coli*, the product of the dsbA gene (Bardwell et al, Cell 67: 581–589 (1991), also can be considered a thioredoxin-like sequence. These four publications are incorporated herein by reference for the purpose of providing information on PI-PLC, ERp72, ADF, and dsbA which are known and available to one of skill in the art.

It is expected from the definition of thioredoxin-like DNA sequence used above that other sequences not specifically identified above, or perhaps not yet identified or published, may be thioredoxin-like sequences either based on the 30% amino acid sequence homology to *E. coli* thioredoxin or based on having three-dimensional structures substantially similar to *E. coli* or human thioredoxin and having an active-site loop functionally and structurally equivalent to the Cys . . . Cys active-site loop of *E. coli* thioredoxin. One skilled in the art can determine whether a molecule has these latter two characteristics by comparing its three-dimensional structure, as analyzed for example by x-ray crystallography or 2- dimensional NMR spectroscopy, with the published three-dimensional structure for *E. coli* thioredoxin and by analyzing the amino acid sequence of the molecule to determine whether it contains an active-site loop that is structurally and functionally equivalent to the Cys . . . Cys active-site loop of *E. coli* thioredoxin. By "substantially similar" in three-dimensional structure or conformation is meant as similar to *E. coli* thioredoxin as is glutaredoxin. In addition a predictive algorithm has been described which enables the identification of thioredoxin-like proteins via computer-assisted analysis of primary sequence (Ellis et al, Biochemistry 31: 4882–91 (1992)). Based on the above description, one of skill in the art will be able to select and identify, or, if desired, modify, a thioredoxin-like DNA sequence for use in this invention without resort to undue experimentation. For example, simple point mutations made to portions of native thioredoxin or native thioredoxin-like sequences which do not effect the structure of the resulting molecule are alternative thioredoxin-like sequences, as are allelic variants of native thioredoxin or native thioredoxin-like sequences.

DNA sequences which hybridize to the sequence for *E. coli* thioredoxin or its structural homologs under either stringent or relaxed hybridization conditions also encode thioredoxin-like proteins for use in this invention. An example of one such stringent hybridization condition is hybridization at 4×SSC at 65° C., followed by a washing in 0.1XSSC at 65° C. for an hour. Alternatively an exemplary stringent hybridization condition is in 50% formamide, 4×XSSC at 42° C. Examples of non-stringent hybridization conditions are 4×XSSC at 50° C. or hybridization with 30–40% formamide at 42° C. The use of all such thioredoxin-like sequences are believed to be encompassed in this invention.

Construction of a fusion sequence of the present invention, which comprises the DNA sequence of a selected peptide or protein and the DNA sequence of a thioredoxin-like sequence, employs conventional genetic engineering techniques. See, Sambrook et al., Molecular Cloning. A Laboratory Manual, 2nd edition, Cold Spring Harbor Laboratory, Cold Spring Harbor, N.Y. (1989). Fusion sequences may be prepared in a number of different ways. For example, the selected heterologous protein may be fused to the amino terminus of the thioredoxin-like molecule. Alternatively, the selected protein sequence may be fused to the carboxyl terminus of the thioredoxin-like molecule. Small peptide sequences could also be fused to either of the above-mentioned positions of the thioredoxin-like sequence to produce them in a structurally unconstrained manner.

This fusion of a desired heterologous peptide or protein to the thioredoxin-like protein increases the stability of the peptide or protein. At either the amino or carboxyl terminus, the desired heterologous peptide or protein is fused in such a manner that the fusion does not destabilize the native structure of either protein. Additionally, fusion to the soluble thioredoxin-like protein improves the solubility of the selected heterologous peptide or protein.

It may be preferred for a variety of reasons that peptides be fused within the active-site loop of the thioredoxin-like molecule. The region on the surface of thioredoxin surrounding the active-site loop has evolved, in keeping with the protein's major function as a non-specific protein disulfide oxido-reductase, to be able to interact with a wide variety of other protein surfaces, and so may be especially tolerant to the presence of inserted sequences. In addition the active-site loop region is bounded by segments of strong secondary structure, which provides many advantages for peptide fusions. Any small peptide inserted into the active-site loop of a thioredoxin-like protein is present in a region of the protein which is not involved in maintaining tertiary structure. Therefore the structure of such a fusion protein is stable. Indeed previous work has shown that *E. coli* thioredoxin can be cleaved into two fragments at a position close to the active-site loop, and yet the tertiary interactions stabilizing the protein remain intact.

The active-site loop of *E. coli* thioredoxin has the sequence $NH_2$- ... $Cys_{33}$-Gly-Pro-$Cys_{36}$ ... COOH. Fusing a selected peptide with a thioredoxin-like protein in the active-site loop portion of the protein constrains the peptide at both ends, reducing the degrees of conformational freedom of the peptide, and consequently reducing the number of possible alternative structures taken by the peptide. The inserted peptide is bound at each end by cysteine residues, which may form a disulfide linkage to each other as they in native thioredoxin and further limit the conformational freedom of the inserted peptide. Moreover, this invention places the peptide on the surface of the thioredoxin-like protein. Thus the invention provides a distinct advantage for use of the peptides in screening for bioactive peptide conformations and other assays by presenting peptides inserted in the active-site loop in this structural context.

Additionally the fusion of a peptide into the loop protects it from the actions of *E. coli* amino- and carboxyl-peptidases. Further, a restriction endonuclease cleavage site RsrII already exists in the portion of the *E. coli* thioredoxin DNA sequence encoding the loop region at precisely the correct position for a peptide gene fusion. (See, McCoy, et al. supra; FIG. 4.) RsrII recognizes the DNA sequence CGG(A/T)CCG leaving a three nucleotide long 5'-protruding sticky end. DNA bearing the complementary sticky ends will therefore insert at this site in only one orientation.

As used herein the term "fusion protein" includes, but is not limited to, any "protein of interest" that is covalently bonded to another protein, e.g., the fusion partner. The cleavage of products of the fusion protein comprise the fusion partner and the protein of interest. As used herein the term "thioredoxin fusion protein" includes, but is not limited to, the expression product of the thioredoxin-like DNA (described supra), and another DNA encoding the protein of interest.

As used herein the term "anion exchange resin" includes, but is not limited to, any type of support to which are bound positively charged pendant groups, such as diethyleaminoethane (DEAE), polyethyleneimine (PEI), or quaternary aminoethane (QAE) groups. The groups may either be positively charged regardless of pH, or positively charged within a specific pH range, being neutral (with no charge) outside of that pH range.

As used herein the term "cation exchange resin" includes, but is not limited to, any type of support to which are bound negatively charged pendant groups, such as sulfonyl, sulfylpropyl (SP), carboxyl, or carboxymethyl (CM) groups. The groups may either be negatively charged regardless of pH, or negatively charged within a specific pH range, being neutral (with no charge) outside of that pH range.

As used herein the term "charged" includes, but is not limited to a chemical species having a non-zero net electrostatic charge, either positive or negative, without regard to the magnitude of the net charge.

As used herein the term "negatively charged" includes, but is not limited to, any chemical species, whether charged or not, that adsorbs to an anion exchange chromatography resin at the pH and ionic strength of the operating buffer; or any chemical species that does not adsorb to a cation exchange chromatography resin at the pH and ionic strength of the operating buffer.

As used herein the term "positively charged" includes, but is not limited to, any chemical species, whether charged or not, that adsorbs to a cation exchange chromatography resin at the pH and ionic strength of the operating buffer; or any chemical species that does not adsorb to an anion exchange chromatography resin at the pH and ionic strength of the operating buffer.

As described in greater detail below, the term "host cell" generally includes any transformed or non-transformed grain negative microorganism.

As used herein, the term "chelator" includes but is not limited to, any compound which will form two or more intermolecular ordinary or coordinate bonds with metal ions in solution, so that one or more heterocyclic rings are formed with each bound metal ion, and includes, but is not limited to, such compounds as ethylenediaminetetraacetic acid (EDTA), diethylenetriaminopentaacetic acid (DPTA), ethylene glycol-bis(2-aminoethyl ether) tetraacetic acid (EGTA), 1,2-cyclohexanediaminetetraacetic acid (CDTA), and citric acid.

As used herein, the term "divalent cation" includes, but is not limited to such species as $Mg^{++}$(magnesium), $Mn^{++}$ (manganese), $Ca^{++}$(calcium) and the like.

As used herein, the term "collecting" includes, but is not limited to for example, the process by which a process stream is pumped through a column of chromatography resin and the unbound fraction (sometimes also referred to as the flow through fraction) is collected While the present method of the invention is exemplified by purification of recombinantly-produced proteins from transformed host cells, the method is also amenable to purification of proteins which are naturally occurring within a cell and can be used generally to purify proteins from any solution, regardless of source.

The following examples illustrate practice of the invention. These examples are for illustrative purposes only and are not intended in any way to limit the scope of the invention claimed. Example 1 describes construction of a fusion protein; Example 2 describes the expression of a fusion protein; Example 3 describes selective release of protein from a cell using chelator; Example 4 relates to removal of the negatively charged molecules from solution; Example 5 describes the selective precipitation with zinc; and Example 6 relates to purification of a fusion protein based upon a difference in pI upon cleavage of the protein of interest from its fusion partner.

EXAMPLE 1
PREPARATION OF FUSION PROTEIN MOLECULE

A thioredoxin-like fusion protein can be made by constructing a fusion DNA comprising a thioredoxin-like sequence linked to a DNA encoding the polypeptide of interest and expressing the DNA construct in an appropriate host cell. For example, a thioredoxin-like fusion molecule of the present invention can be prepared using E. coli thioredoxin as the thioredoxin-like sequence and recombinant IL-11 (Paul et al., Proc. Natl. Acad. Sci. U.S.A. 87:7512-7516 (1990); see also, copending U.S. patent applications Ser. No. 07/526,474, and Ser. No. 07,441,100 and PCT Patent publication WO91/07495, published May 30, 1991 incorporated herein by reference) as the selected heterologous protein. The E. coli thioredoxin (trxA) gene (McCoy, et al., supra.) was cloned based on its published sequence and employed to construct various related E. coli expression plasmids using standard DNA manipulation techniques, described extensively by Sambrook, et al., Molecular Cloning. A Laboratory Manual, 2nd edition, Cold Spring Harbor Laboratory, Cold Spring Harbor, N.Y. (1989).

A first expression plasmid pALtrxA-781 was constructed containing the E. coli trxA gene without fusion to another sequence. This plasmid further contained sequences which are described in detail below for the related IL-11 fusion plasmid. This first plasmid, which directs the accumulation of >10% of the total cell protein as thioredoxin in an E. coli host strain GI724, was further manipulated as described below for the construction of a trxA/IL-11 fusion sequence.

Alternatively, a thioredoxin-like molecule modified to include metal-binding/chelating amino acid residues, such as, e.g., histidine residues at positions 2, 31 and 63, or, alternatively, at positions 31 and 63, was prepared as described in co-pending U.S. Ser. No. 08/165,301, incorporated herein by reference, using standard DNA manipulation techniques (reference above).

The entire sequence of the related plasmid expression vector, pALtrxA/EK/IL11Δ Pro-581 (McCoy, et al., supra., as illustrated in FIG. 1) and contains the following principal features:

NuCleotides 1-2060 contain DNA sequences originating from the plasmid pUC-18 (Norrander et al., Gene 26: 101-106 (1983)) including sequences containing the gene for β-lactamase which confers resistance to the antibiotic ampicillin in host E. coli strains, and a colE1-derived origin of replication. Nucleotides 2061-2221 contain DNA sequences for the major leftward promoter (pL) of bacteriophage λ (Sanger et al., J. Mol. Biol. 162:729-773 (1982)), including three operator sequences, $O_L1$, $O_L1$, $O_L2$ and $O_L3$. The operators are the binding sites for λcI repressor protein, intracellular levels (if which control the amount of transcription initation from pL. Nucleotides 2222-2241 contain a strong ribosome binding sequence derived from that of gene 10 of bacteriophage T7 (Dunn and Studier, J. Mol. Biol. 166:477-535 (1983)).

Nucleotides 2242-2568 contain a DNA sequence encoding the E. coli thioredoxin protein (Lim et al., J. Bacteriol. 163:311-316 (1985)). There is no translation termination codon at the end of the thioredoxin coding sequence in this plasmid.

Nucleotides 2569-2583 contain DNA sequence encoding the amino acid sequence for a short, hydrophilic, flexible spacer peptide "-GSGSG-". Nucleotides 2584-2598 provide DNA sequence encoding the amino acid sequence for the cleavage recognition site of enterokinase (EC 3.4.4.8), "-DDDDK-"(Maroux et al., Biol. Chem. 246:5031-5039 (1971)).

As an alternative embodiment, a single additional codon can be inserted into the linker sequence of the plasmid to introduce a specific site for chemical cleavage of the thioredoxin-IL-11 fusion protein by hydroxylamine. The nucleotide triplet introduced between residues 2598 and 2599 of pALtrxA/EK/IL11ΔPro-581, "-ATT-", encodes an asparagine residue. This asparagine, in combination with the glycine residue immediately following, comprises a new hydroxylamine cleavage will occur between the asparagine and glycine residues. As an additional feature of this alternative embodiment two naturally occurring asparagine residues present in wild-type thioredoxin, amino-acids 84 and 107, may be altered to glutamine by standard techniques to remove two other unwanted hydroxylamine cleavage sites, thus reducing secondary hydroxylamine cleavage products which could hamper subsequent purification procedures.

Nucleotides 2599-3132 contain DNA sequence encoding the amino acid sequence of a modified form of mature human IL-11 (Paul et al., Proc. Natl. Acad. Sci. USA 87:7512-7516 (1990)), deleted for the N-terminal prolyl-residue normally found in the natural protein. The sequence includes a translation termination codon at the 3'-end of the IL-11 sequence.

Nucleotides 3133-3159 provide a "Linker" DNA sequence containing restriction endonuclease sites. Nucleotides 3160-3232 provide a transcription termination sequence based on that of the E. coli aspA gene (Takagi et al., Nucl. Acids Res. 13:2063-2074 (1985)). Nucleotides 3233-3632 are DNA sequences derived from pUC-18.

As described in Example 2 below, when cultured under the appropriate conditions in a suitable E. coli host strain, this plasmid vector can direct the production of high levels (approximately 10% of the total cellular protein) of a thioredoxin/IL-11 fusion protein. By contrast, when not fused to thioredoxin, IL-11 accumulated to only 0.2% of the total cellular protein when expressed in an analogous host/vector system.

EXAMPLE 2
EXPRESSION OF A FUSION PROTEIN

A thioredoxin/IL-11 fusion protein is produced according to the following protocol using the plasmid constructed as described in Example 1. pALtrxA/EK/IL11ΔPro-581 is transformed into the E. coli host strain GI724 (F⁻, lacI$^q$, lacP$^{L8}$, ampC::λcI$^+$) by the procedure of Dagert and Ehrlich, Gene 6:23 (1979). The untransformed host strain E. coli GI724 was deposited with the American Type Culture Collection, 12301 Parklawn Drive, Rockville, MD. on Jan. 31, 1991 under ATCC No. 55151 for patent purposes pursuant to applicable laws and regulations. Transformants are selected on 1.5% w/v agar plates containing IMC medium, which is composed of M9 medium (Miller, "Experiments in Molecular Genetics", Cold Spring Harbor Laboratory, New York (1972)) containing 1 mM MgSO$_4$ and supplemented with 0.5% w/v glucose, 0.2% w/v casamino acids and 100 μg/ml ampicillin.

GI724 contains a copy of the wild-type λcI repressor gene stably integrated into the chromosome at the ampC locus, where it has been placed under the transcriptional control of Salmonella typhimurium trp promoter/operator sequences. In GI724, λcI protein is made only during growth in tryptophan-free media, such as minimal media or a minimal medium supplemented with casamino acids such as IMC, described above. Addition of tryptophan to a culture of GI724 will repress the trp promoter and turn off synthesis of λcI, gradually causing the induction of transcription from pL promoters if they are present in the cell.

GI724 transformed with pALtrxA/EK/IL11 Pro-581 is grown at 30° C. to an A$_{600}$ of 20 in IMC medium (with 3×MgSO$_4$). The glucose concentration of the culture is maintained at approximately 0.2% (wt./vol.). The pH is maintained at 7.0 with 7.5M ammonium hydroxide. Tryptophan is added to a final concentration of 100 μg/ml and the culture incubated for a further 4 hours at 37° C. During this time, thioredoxin/IL-11 fusion protein accumulated to approximately 10% of the total cell protein.

All of the fusion protein is found to be in the soluble cellular fraction, and is purified, as follows, for the following analyses. Cells are lysed in a french pressure cell at 20,000 psi in 50 mM HEPES pH 8.0, 1 mM phenylmethylsulfonyl fluoride. The lysate is clarified by centrifugation at 15,000×g for 30 minutes and the supernatant loaded onto a QAE-Toyopearl column. The flow-through fractions are discarded and the fusion protein eluted with 50 mM HEPES pH 8.0, 100 mM NaCl. The eluate is adjusted to 2M NaCl and loaded onto a column of phenyl-Toyopearl. The flow-through fractions are again discarded and the fusion protein eluted with 50 mM HEPES pH 8.0, 0.5M NaCl.

The fusion protein is then dialyzed against 25 mM HEPES pH 8.0 and is >80% pure at this stage. By T 1165 bioassay (Paul et al., supra) the purified thioredoxin/IL-11 protein exhibits an activity of 8×10$^5$U/mg. This value agrees closely on a molar basis with the activity of 2×10$^6$U/mg found for COS cell-derived IL-11 in the same assay. One milligram of the fusion protein is cleaved at 37° C. for 20 hours with 1000 units of bovine enterokinase (Leipnieks et al., J. Biol. Chem. 254:1677–1683 (1979)) in 1 ml 10 mM Tris-Cl (pH 8.0)/10 mM CaCl$_2$. IL-11 is recovered from the reaction products by passing them over a QAE-Toyopearl column in 25 mM HEPES pH 8.0, where IL-11 is found in the flow-through fractions. Uncleaved fusion protein, thioredoxin and enterokinase remain bound on the column. The IL-11 prepared in this manner has a bioactivity in the T1165 assay of 2.5×10$^6$ U/mg. Its physical and chemical properties are determined as follows:

(1) Molecular Weight

The molecular weight of the IL-11 is found to be about 21 kD as measured by 10% SDS-PAGE under reducing conditions (tricine system) in accordance with the methods of Schagger, et al., Anal Biochem. 166:368–379 (1987). The protein ran as a single band.

(2) Endotoxin Content

The endotoxin content of the IL-11 is found to be less than 0.1 nanogram per milligram IL-11 in the LAL (Limulus amebocyte lysate, Pyrotel, available from Associates of Cape Cod, Inc., Woods Hole, Mass., U.S.A.) assay, conducted in accordance with the manufacturer's instructions.

(3) Isoelectric Point

The theoretical isoelectric point of IL-11 is pH 11.70. As measured by polyacrylamide gel isoelectric focusing using an LKB Amlholine PAGplate with a pH range from 3.5 to 9.5, the IL-11 runs at greater than 9.5. An exact measurement can not be taken because IL-11 is too basic a protein for accurate pI determinations.

(4) Fluorescence Absorption Spectrum

The fluorescence absorption spectrum of the IL-11, as measured on a 0.1% aqueous solution in a 1 cm quartz cell shows an emission maximum at 335–337 nm.

(5) UV Absorption

UV absorption of the IL-11 on a 0.1% aqueous solution in a 1 cm quartz cell showed an absorbance maximum at 278–280 nm.

6) Amino Acid Composition

The theoretical amino acid composition for IL-11, based on its amino acid sequence is as follows:

| Amino Acid | Number | Mole % |
| --- | --- | --- |
| Ala | 20 | 11.3 |
| Asp Acid | 11 | 6.22 |
| Cysteine | 0 | 0 |
| Glu | 3 | 1.70 |
| Phe | 1 | 0.57 |
| Gly | 14 | 7.91 |
| His | 4 | 2.26 |
| Ile | 2 | 1.13 |
| Lys | 3 | 1.70 |
| Leu | 41 | 23.16 |
| Met | 2 | 1.13 |
| Asn | 1 | 0.57 |
| Pro | 21 | 11.86 |
| Gln | 7 | 3.96 |
| Arg | 18 | 10.17 |
| Ser | 11 | 6.22 |
| Thr | 9 | 5.09 |
| Val | 5 | 2.83 |
| Trp | 3 | 1.70 |
| Tyr | 1 | 0.57 |

A sample of homogenous IL-11 is subjected to vapor phase hydrolysis as follows: 6 N HCl and 2N phenol reagent were added to an hydrolysis vessel in which tubes containing 45 μl of 1:10 diluted (w/H$_2$O) IL-11 concentrated to dryness are inserted. Samples are sealed under vacuum and hydrolyzed for 36 hours at 110° C. After the hydrolysis, samples are dried and resuspended in 500 μl Na-S sample dilution buffer. Amino acid analysis was performed on a Beckman 7300 automated amino acid analyzer. A cation exchange column is used for separation of amino acids following post-column derivatization with ninhydrin. Primary amino acids are detected at 570 nm and secondary amino acids are detected at 440 nm. Eight point calibration curves are constructed for each of the amino acids.

Because certain amino acids are typically not recovered, results for only 5 amino acids are given below. Since the hydrolysis is done without desalting the protein, 100% recovery was achieved for most of the amino acids.

The relative recovery of each individual amino acid residue per molecule of recombinant IL-11 is determined by normalizing GLX =10 (the predicted number of glutamine and glutamic acid residue in IL-11 based on cDNA sequence). The value obtained for the recovery of GLX in picomoles is divided by 10 to obtain the GLX quotient. Dividing the value obtained for the recovery in picomoles of each amino acid by the GLX quotient for that sample gives a number that represents the relative recovery of each amino acid in the sample, normalized to the quantitative recovery of GLX residues. The correlation coefficient comparing the expected versus the average number of residues of each amino acid observed is greater than 0.985, indicating that the number of residues observed for each amino acid is in good agreement with that predicted sequence.

| Amino Acids | No. of Residues Calculated | No. of Residues Expected | Correlation Coefficient |
|---|---|---|---|
| 1 Asp | 12.78 | 12 | |
| 2 Glu | 10.00 | 10 | |
| 3 Gly | 12.80 | 14 | 0.9852 |
| 4 Arg | 16.10 | 18 | |
| 5 Pro | 18.40 | 21 | |

(7) Amino Terminus Sequencing

IL-11 (buffered in 95% acetonitrile TFA) is sequenced using an ABI 471A protein sequencer (ABI, Inc.) in accordance with the manufacturer's instructions. Amino terminus sequencing confirms that the thioredoxin fusion protein produced IL-11 contains the correct IL-11 amino-acid sequence, and only one amino terminus is observed.

(8) Peptide Mapping

The IL-11 is cleaved with Endoproteinase Asp-N (Boehringer Mannheim) (1:500 ratio of Asp-N to IL-11) in 10 mM Tris, pH 8, 1M urea and 2 mM 4-aminobenzamidine dihydrochloride (PABA), at 37° C. for 4 hours. The sample is then run on HPLC on a C4 Vydac column using an A buffer of 50 mM NaHPO$_4$, pH 4.3, in dH$_2$O, a B buffer of 100% isopropanol with a gradient at 1 ml/min from 100%A to 25%A and 75%B (changing at 1%/minute). The eluted peptide fragments are then sequenced using an ABI 471A protein sequencer (ABI, Inc.) in accordance with the manufacturer's instructions. The peptide map confirmed that the IL-11 produced from the thioredoxin fusion protein contains the expected IL-11 N-terminal and C-terminal sequences.

(9) Solubility

IL-11 protein is tested for solubility in the substances below with the following results:

| | |
|---|---|
| Water | very soluble |
| Ethyl Alcohol | very soluble |
| Acetone | very soluble |
| 1M sodium chloride | very soluble |
| 10% sucrose | very soluble |

(10) Sugar Composition and Protein/Polysaccharide Content in %

The absence of sugar moieties attached to the polypeptide backbone of the IL-11 protein is indicated by its amino acid sequence, which contains none of the typical sugar attachment sites.

When the fusion construct is made having a hydroxylamine cleavage site, cleavage is carried out as follows. A thioredoxin/IL-11 fusion protein, modified as described above to contain a hydroxylamine cleavage site between the thioredoxin and IL-11 sequences, is chemically cleaved in a reaction with hydroxylamine. The modified fusion protein at a concentration of 2.5 mg/ml is cleaved in a reaction with 1M hydroxylamine in 0.1M CHES buffer at pH 9.7. The reaction is allowed to proceed for 11 h at 35° C., and is terminated by cooling to 4° C. and lowering the pH to pH 8.0 by the addition of Tris-HCl (pH 7.3).

EXAMPLE 3
SELECTIVE PROTEIN RELEASE

The selective release of a fusion protein from the cytoplasm of intact, harvested, *E. coli* cells occurs as a consequence of destabilization of the outer cell membrane by a chelator such as TRIS/EDTA. The chelating agent, EDTA, is thought to permeabilize grain-negative bacteria by binding divalent cations that stabilize lipopolysaccharides (LPS) in the outer membrane. While in a presently preferred embodiment, the cells are first harvested prior to the release step, it is also possible to simply add chelator directly to the cell culture medium. An excess of chelator is added to ensure the supply of chelator is not exhausted by any entities present in the culture medium which are bound by chelator.

Selective release is accomplished, for example, by addling a solution of 680 mM TRIS, 240 mM EDTA, pH 8.0 to the harvest/release vessel containing chilled (3° C.) harvested cells. The final buffer composition is 50 mM Tris and 15 mM EDTA and the *E. coli* concentration in the resulting suspension is 250 grams (wet cell weight) per liter. The suspension is heated to 37° C. and incubated for 30 minutes. Base, such as 5N NaOH, is used to ad just the pH of the release suspension to about pH 8.5. This treatment releases fusion protein and a spectrum of constitutive *E. coli* proteins. Approximately 50% of the total cell protein including greater than 80% of the protein of interest and 15 % of cellular DNA is released. The quantity of protein liberated from the cells after addition of the TRIS/EDTA solution to the harvest cell suspension is monitored by Branford assay (Bradford, M., Analytical Biochemistry 72:248–254 (1976)).

Table 2 lists the controlled operating parameters for this release step including preferred targets as well as preferred ranges. One skilled in the art will appreciate that broader ranges will be similarly effective. Table 3 lists the monitored operating parameters.

TABLE 2

Release Step: Controlled Operating Parameters

| Parameter | Preferred Target | Preferred Range |
|---|---|---|
| Release vessel temperature | 37° C. | 32–42° C. |
| Release vessel agitation | 170 rpm | 160–180 |
| Release vessel pH | 8.5 | 8.0–8.8 pH |
| Release time | 30 min | 20–60 min |

TABLE 3

Release Step: Monitored Operating Parameters

| Parameter | Preferred Target |
|---|---|
| Total protein Released (Bradford at 30 min) | 12 mg/mL |
| Total Protein Relative to Lysis | 50% |
| Total DNA Released | 300 ug/ml |

TABLE 3-continued

| Release Step: Monitored Operating Parameters | |
|---|---|
| Parameter | Preferred Target |
| Total DNA Relative to Lysis | 15% |

The release process also liberates polyanionic species such as DNA, RNA, and LPS from the cells. The presence of these non-proteinaceous components in the release suspension renders it turbid and relatively unfilterable. They are removed via the clarification step, as described in Example 4.

EXAMPLE 4
CLARIFICATION AND REMOVAL OF NEGATIVELY CHARGED MOLECULES

Process material is clarified by selective precipitation of non-proteinaceous components and results in a filterable process stream. Precipitation is initiated by sequential addition of 2 M $MgCl_2$, 95% ethanol, and 2M $CaCl_2$ to the harvest/release vessel containing the release suspension. The concentration of reactants in the resulting suspension is 125 mM $MgCl_2$, 75 mM $CaCl_2$, and 14% (volume/volume%) ethanol. The precipitation, which is executed for a minimum of five minutes, is controlled at 32° C. and a pH of 7.5. The concentration of reactants and the pH, temperature, and reaction time are controlled within the limits presented in Table 4. Non-proteinaceous components are removed from suspension by continuous centrifugation at a maximum centrifugal force of 15,000×g, a residence time of 1.4 minutes, and a sedimentation distance of 0.5 mm. If desired, residual particulates can be removed from the supernatant stream by in-line 0.5-μm filtration. Greater than 80% of the DNA and 90% the LPS previously in solution is removed. Recovery of the protein of interest is circa 80%. The protein concentration (Bradford assay) and turbidity ($OD_{600}$) are monitored as indicators process performance.

Table 4 lists the controlled operating parameters for this clarification step including preferred targets as well as preferred ranges. One skilled in the art can readily appreciate that broader ranges will be similarly effective. Table 5 lists performance characteristics of monitored parameters.

TABLE 4

| Clarification Step: Control Operating Parameters | | |
|---|---|---|
| Parameter | Preferred Target | Preferred Range |
| 2 M $MgCl_2$ | 0.083 (v/v)* | 0.066–0.10 (v/v)* |
| 2 M $CaCl_2$ | 0.050 (v/v)* | 0.033–0.068 (v/v)* |
| 95% Ethanol | 0.20 (v/v)* | 0.17–0.23 (v/v)* |
| Clarification vessel/Temperature | 32° C. | 20–37° C. |
| Clarification vessel/Agitation | 220 rpm | 210–230 rpm |
| Clarification vessel/pH | 7.5 | 6.8–7.8 |
| Clarification time | 5 min | 5–30 min |

*: volume reagent/volume release suspension

TABLE 5

| Clarification Step: Monitored Operating Parameters | |
|---|---|
| Parameter | Preferred Target |
| Turbidity of bulk filtered supernatant ($OD_{600}$) | <0.32 $OD_{600}$ |

TABLE 5-continued

| Clarification Step: Monitored Operating Parameters | |
|---|---|
| Parameter | Preferred Target |
| Total protein in bulk filtered supernatant (Bradford assay) | 6 mg/mL |
| Fusion protein concentration in bulk filtered supernatant (Reversed Phase Analysis) | 2 mg/mL |
| Total DNA after clarification | 30 ug/ml |
| Fold LPS removal | 1000 fold |

EXAMPLE 5
SELECTIVE PRECIPITATION

After the clarification step, optionally, it is possible to use a selective precipitation of the protein of interest. This is accomplished by adding 1 volume of 1M $ZnCl_2$ to 19 volumes of 4° C. clarified supernatant. The pH of the suspension is maintained at 7.0 with 2.5M Tris base. After incubation of the suspension for 15 minutes, the resulting precipitate is recovered by continuous centrifugation at a maximum centrifugal force of 15,000×g, a sedimentation distance of 2.5 cm, with a residence time of 3 minutes. The recovered precipitate is subsequently frozen in liquid nitrogen and stored frozen at −80° C. The precipitate is subsequently solubilized in 20 mM Tris/100 mM EDTA (pH=8.0) at 20° C. at a ratio of 100 grams of precipitate per liter buffer. Greater than 75% of the protein of interest is recovered over the process as measured by reversed phase HPLC.

EXAMPLE 6
PURIFICATION

After the clarification step (Example 4), a processing method which can be used (alternative to selective precipitation (Example 5)) is ultrafiltration/diafiltration using tangential-flow membrane filtration. This step concentrates the clarified fusion protein solution and exchanges the protein into a low-ionic strength buffer that is suitable for ion exchange chromatography. The membrane used in the tangential-flow device serves as a porous filter that separates substances on the basis of molecular weight. Solution components of high molecular weight (such as proteins) are retained by the membrane, and components of low molecular weight (such as inorganic salts and buffer compounds) freely pass through the porous membrane structure and are removed in the permeate.

When a replacement buffer is added to the tangential-flow retentate at a rate approximately equal to the rate at which the buffer is drawn through the membrane and discarded, the initial buffer is continuously diluted (protein diafiltration). Under these conditions, compounds of low molecular weight are readily exchanged and the protein concentration remains constant. The addition of five retentate volumes of buffer results in ≧99% replacement of the initial buffer. When buffer is drawn from the tangential-flow device at a rate faster than that at which replacement buffer is added to the retentate, the protein solution is concentrated.

The first Ultrafiltration/Diafiltration Step (UFDF #1) of the recovery process concentrates and buffer exchanges the fusion protein present in the filtered clarified supernatant. This process step uses a series of plate-and-frame membrane cartridges for example, Millipore Pellicon regenerated cellulose cassette filters, with a membrane molecular weight cutoff of ≦10 kDa. In addition, in-line prefilters (Millipore Milligard, 1.2 μm pore size) are used for continuous filtration of the retentate to remove any particulates which could foul the membranes. The temperature target for the step is 8° C.

Before use, the ultrafiltration skid and membranes are flushed with 20 mM Tris, 0.3M NaCl, pH 8.0 to equilibrate the system. A solution of 4M NaCl is added at a ratio of 9.32% (w/v) to the filtered clarified supernatant (FCS) in a holding tank, which is then mixed before processing begins. The FCS is pumped across the membrane at a positive transmembrane pressure, and the retentate is recirculated to the vessel while the permeate is directed to waste. The FCS is concentrated approximately three fold (Concentration I). After Concentration I is completed, a diluent stream of 20 mM Tris, 0.3M NaCl, pH 8.0 is added to the holding vessel at a flow rate equal to the permeate flow rate (Diafiltration 1). In this manner, the buffer of the FCS is continuously diluted with the diluent buffer. When the total permeate volume is ≧5 times the Concentration I final volume, Diafiltration I is complete. Over 99% of the low-molecular weight solutes present in the original buffer are removed.

When Diafiltration I is completed, a diluent stream of 20 mM Tris, pH 8.0 is added to the retentate vessel at a flow rate equal to the permeate flow rate (Diafiltration II). When the total permeate volume is ≧5 times the Concentration I final volume, Diafiltration II is complete. After Diafiltration II is completed, the retentate is then concentrated an additional 10% (Concentration 11). The equipment is flushed with a sufficient volume of 20 mM Tris, pH 8.0, to wash out the concentrated protein solution, bringing the total pool volume to approximately 0.4 times the starting volume of FCS. The UFDF #1 pool is pumped out of the vessel and filtered through an autoclaved 0.2-μm filter attached to a clean, autoclaved pressure vessel. The filtered pool is stored at 2°–10° C. before further processing.

The average recovery of fusion protein from this step is 89%. Table 6 lists the operating parameters that are controlled during this step.

TABLE 6

Operating Parameters Controlled for the UFDF #1 Step

| Procedure | Parameter | Recommended Target |
|---|---|---|
| All procedures | Inlet feed pressure | 80 psig |
| | Retentate pressure | 40 psig |
| | Pressure drop over pre-filters | ≦25 psig |
| | Holding tank temperature | 8° C. |
| Equilibration | Retentate and permeate pH | 8.0 |
| | Retentate and permeate conductivity | 17–23 mS/cm |
| Concentration I | Final volume | 0.3 × starting volume of FCS |
| Diafiltration I | Retentate and permeate pH | 8.0 |
| | Permeate volume | ≧5 × Concentration 1 final volume |
| | Permeate conductivity | 17–23 mS/cm |
| Diafiltration II | Retentate and permeate pH | 8.0 |
| | Permeate volume | ≧5 × Concentration 1 final volume |
| | Permeate conductivity | ≦2 mS/cm |
| Concentration II | Final volume after flush | 0.4 × starting volume of FCS |

The purification of protein of interest, for example rhIL-11, involves, first, purification of the fusion protein away from positively charged contaminants; second, cleavage of the fusion protein into its components, namely rhIL-11 and thioredoxin; and third, purification of the protein of interest, e.g., rhIL-11.

Purification of the fusion form of the protein is accomplished with two ion-exchange chromatography steps. After cleavage of the fusion protein, two additional ion-exchange chromatography steps are used to purify the cleaved form of the fusion protein. In the first chromatography step, an anion-exchange resin, for example Toyopearl QAE, is used to adsorb the fusion protein (and other negatively charged proteins) from the process stream, and in the second step, a cation-exchange resin, for example S Sepharose Fast Flow, is used to adsorb positively charged proteins from the process stream while fusion protein flows through the column.

Toyopearl QAE 550C, is a strong anion-exchange resin composed of a rigid polymeric support that is covalently derivatized with a quaternary amine. Proteins and polyionic substances (for example, polynucleotides and lipopolysaccharides) with a net negative charge at the pH of operation bind to this resin as a function of solution ionic strength. The Toyopearl QAE resin is used to adsorb fusion protein from the product stream under low-salt conditions through ionic interactions. Elution of the thioredoxin/rhIL-11 fusion protein is accomplished by both lowering the pH and increasing the ionic strength in the appropriate buffer. Appropriate eluants include 20–100 mM Tris buffers at pH 7.5–8.5 containing 100–500 mM NaCl, or 50–200 mM Histidine buffers at pH 5.5–6.6, containing 0–150 mM NaCl.

S Sepharose Fast Flow is a strong cation-exchange chromatography gel composed of a cross-linked agarose matrix that is derivatized with sulphonate groups. Contaminants, both proteins and polyionic substances with isoelectric points higher than the pH of the running buffer, bind to S Sepharose Fast Flow via charge interactions.

The fusion protein is bound to and then eluted from the QAE column, passed through the S Sepharose Fast Flow column, and recovered in the S Sepharose Fast Flow unbound fraction. The conditions for elution of the QAE column have been optimized to minimize binding of thioredoxin/rhIL-11 fusion protein to the S Sepharose Fast Flow resin, while contaminants with a higher pI than the fusion protein bind to the S Sepharose Fast Flow column and are removed from the process stream.

Both the Toyopearl QAE 550C column and the S Sepharose Fast Flow column are equilibrated and run at ambient temperature. The S Sepharose Fast Flow column is equilibrated with 150 mM Histidine, 150 mM NaCl, pH 6.2 followed by a second equilibration with 75 mM Histidine, 75 mM NaCl, pH 6.2.Next the Toyopearl QAE column is equilibrated separately from the S Sepharose Fast Flow column with 20 mM Tris pH 8.0.The UFDF #1 concentrate, as described supra, is then loaded onto the equilibrated Toyopearl QAE column at a linear velocity of ≦1.5 cm/min After the load is completed, the Toyopearl QAE column is washed with 20 mM Tris, pH 8.0 at ≦1.5 cm/min. The QAE column is then eluted with 75 mM NaCl, 75 mM Histidine, pH 6.2 at ≦1.0 cm/min. As the protein begins to elute from the QAE column, the column outlet is connected to the S Sepharose Fast Flow column. The tandem-column eluate peak is collected as a single pool.

Thioredoxin/rhIL-11 fusion protein elutes from the columns as a peak of approximately 5 column volumes. (The column volume is based on the dimensions of the Toyopearl QAE column.) Table 7 lists the operating parameters that are routinely monitored during this step. The average yield of thioredoxin/rhIL-11 fusion protein from this step is 91%.

TABLE 7

Operating Parameters Monitored for the
Toyopearl QAE/S Sepharose Fast Flow Step

| Procedure | Parameter | Preferred Target |
|---|---|---|
| Column Packing: Toyopearl QAE 550C | Bed height | 15–19 cm |
| Column Packing: S Sepharose FF | Bed height | 10–15 cm |
| Equilibration: Toyopearl QAE column | linear velocity[a] | ≦1.5 cm/min |
| | pH | 8.0 ± 0.2 |
| | volume[b] | ≧4 column volumes |
| Equilibration: S Sepharose FF column | linear velocity[a] | ≦4 cm/min |
| | pH (equilibration #1) | 6.2 ± 0.2 |
| | volume[b] | ≧3 column volumes |
| | pH (equilibration #2) | 6.2 ± 0.2 |
| | volume[b] | ≧3 column volumes |
| Load: | volume[a] | 1–2 column volumes |
| UFDF #1 Concentrate | linear velocity[a] | ≦1.0 cm/min |
| Wash: | linear velocity[a] | ≦1.5 cm/min |
| Toyopearl QAE column | volume | 3–4 column volumes |
| Elution | linear velocity[a] | ≦1.0 cm/min |

[a]Flow rate for the QAE column equilibration and load volume for the QAE column are based on the dimensions of the Toyopearl QAE column.
[b]Column equilibration is continued with additional buffer if the pH is out of the target range.
[c]Flow rate for the S Sepharose column equilibration is based on the dimensions of the S Sepharose column Following purification of the fusion protein by QAE Toyopearl and S Sepharose Fast Flow chromatography, the protein is chemically cleaved, in this example at the asparaginyl-glycyl peptide bond in the fusion linkage sequence, to generate rhIL-11 and thioredoxin.

Cleavage of the asparaginyl-glycyl peptide bond under mildly basic conditions using hydroxylamine as the nucleophilic reagent is well documented and a general method has been described (Bornstein, P., and Baliain, G. Cleavage at Asn-Gly bonds with hydroxylamine. Meth. Enzymol. 47(E) :132–145 (1977)). The asparaginyl-glycyl peptide bond is particularly sensitive to hydroxylaminolysis, although asparaginyl-leucyl, asparaginyl-methionyl, and asparaginyl-alanyl cleavages have been reported and may occur relatively slowly. Bornstein, supra.

The Toyopearl QAE/S Sepharose FF eluate pool is added to the cleavage reaction vessel. The hydroxylamine cleavage solution, 3.0M hydroxylamine-HCl, 0.3M CHES, pH 9.7,is added to the vessel at a volume equal to one-half of the volume of the Toyopearl QAE/S Sepharose FF eluate, to produce a final reaction mixture concentration of 1.0M hydroxylamine-HCl and 0.1 M CHES. The pH of the mixture is adjusted to 9.3 (measured at 35° C.) by addition of 10 N NaOH and the temperature is brought to approximately 35° C.

After 9 hours of gentle agitation, the cleavage reaction is ended by reducing the temperature and pH of the reaction mixture. The temperature of the reaction mixture is lowered to ≦8° C. while the pH of the mixture is controlled at 9.3 by addition of a neutralization solution, 2.0M TRIS, pH 7.3. After cooling, additional neutralization solution is added until a volume equal to one-fifth of the volume of the reaction mixture has been added. The neutralized cleavage mixture is stored at ≦8 ° C. before further processing. The cleavage reaction operating parameters are detailed in Table 8.

The extent of thioredoxin/rhIL-11 fusion protein cleavage averages approximately 73%. The most prominent proteins present in the process stream following the cleavage reaction are residual, uncleaved thioredoxin/rhIL-11 fusion protein and the two cleavage products, rhIL-11 and thioredoxin.

TABLE 8

Operating Parameters for the Hydroxylamine Cleavage Step

| Procedure | Parameter | Preferred Target |
|---|---|---|
| Cleavage start | volume of cleavage solution | 0.5 × load volume |
| | agitation rate[a] | 15 rpm |
| | starting pH[b] | 9.3 |
| | temperature | 35° C. |
| | time | 9 hr |
| Cleavage cool-down | pH | 9.3 |
| | final temperature | ≦8° C. |
| Cleavage end | total volume of neutralization solution | 0.2 × total reaction mixture volume |

[a]Agitation rate after all solutions have been added and the proper temperature and pH have been attained.
[b]The pH is determined at 35° C.

Following chemical cleavage of the fusion protein into its component parts of rhIL-11 and thioredoxin, the process stream is concentrated and buffer exchanged into a lower ionic strength buffer using a second ultrafiltration/diafiltration step with tangential-flow membrane filtration. The second ultrafiltration/diafiltration step (UFDF #2) uses a series of plate-and-frame membrane cartridges, for example, Millipore Pellicon regenerated cellulose cassette filters, with a MW cutoff of ≦10 kDa. In addition, in-line prefilters (Millipore Milligard, 1.2 µm pore size) are used for continuous filtration of the retentate to remove any particulates which could foul the membranes. The process step is carried out at a target temperature of ≦8° C. Before use, the ultrafiltration skid and membranes are equilibrated with 20 mM Tris, 0.2 M NaCl, pH 8.0. After membrane equilibration, the cleavage mixture is pumped from the holding vessel across the membrane at a positive transmembrane pressure. The retentate is recirculated to the holding vessel and the permeate stream is directed to waste. This concentrates the rhIL-11 present in the cleavage reaction mixture, and reduces the initial volume by a factor of approximately 6.5.

After concentration is completed, a diluent stream of 20 mM Tris, 0.2M NaCl, pH 8.0 is added to the retentate vessel at a flow rate equal to the permeate flow rate. In this manner, the cleavage reaction buffer is continuously diluted with the diluent buffer. This diafiltration process is continued until the permeate volume is at least five times the concentrated retentate volume. After diafiltration is completed, the ultrafiltration equipment is flushed with sufficient 20 mM Tris, 0.2M NaCl, pH 8.0 to wash out the concentrated protein solution, (approximately 30–40% of the concentrate volume), and the rhIL-11 pool (concentrated solution and flush) is stored in the holding vessel until the next processing step begins. The average recovery of rhIL-11 from this step is 89%. Table 9 lists the operating parameters that are controlled during this step.

TABLE 9

Operating Parameters Controlled for the UFDF #2 Step

| Procedure | Parameter | Recommended Target |
|---|---|---|
| All procedures | Inlet feed pressure | ≦30 psig |
| | Retentate pressure | 10 psig |
| | Holding tank temperature | 2° C. |
| | Pressure drop over pre-filters | ≦60 psig |
| Concentration Diafiltration | Final volume | 0.15 × starting volume |
| | Permeate volume | ≧5 times the retentate volume |

Following the UFDF #2 step, the rhIL-11 is purified with two ion-exchange chromatography steps. In the first step, a cation-exchange resin, in this example CM Sepharose Fast Flow, is used to adsorb the rhIL-11 from the process stream. All steps are performed at a temperature of 2°–8° C. The column is first equilibrated with a buffer containing 20 mM Tris, 0.5 M NaCl, pH 8.0,and then is equilibrated with a buffer containing 20 mM Tris, pH 8.0. The unpurified rhIL-11 pool is pumped through the CM Sepharose column at a velocity of ≦3.2 cm/min. The column is then washed with a solution of 0.15M Glycine, pH 9.5. The CM Sepharose FF column is eluted with 0.15M Glycine, 0.15M NaCl, pH 9.5 into a collecting vessel that contains a specified volume of purified water at ambient temperature for dilution of the peak. The column eluate peak is collected as a single pool, to which additional purified water at ambient temperature is added to achieve a final dilution of one part elution peak with 3 parts purified water. The recovery of rhIL-11 from this step averages approximately 75%. The column operating parameters are detailed in Table 10.

TABLE 10

Operating Parameters for CM Sepharose Fast Flow

| Procedure | Parameter | Preferred Value |
|---|---|---|
| Column Packing: CM Sepharose FF | Bed height | 11–13 cm |
| Equilibration 1 | linear velocity | ≦3.2 cm/min |
|  | pH | 7.8–8.2 |
|  | volume* | ≧3.5 column volumes |
|  | conductivity | ≦30 mS/cm |
| Equilibration 2 | linear velocity | ≦3.2 cm/min |
|  | pH | 7.8–8.2 |
|  | volume* | ≧6 column volumes |
|  | conductivity | ≦4 mS/cm |
| Load | linear velocity | ≦3.2 cm/min |
|  | volume | 4–5 column volumes |
| Dilution of load | volume | 4 × load volume |
|  | conductivity | ≦4 mS/cm |
| Wash | linear velocity | ≦3.2 cm/min |
|  | pH | 9.3–9.7 |
|  | volume | ≧10 column volumes |
|  | conductivity | ≦2 mS/cm |
| Elution | linear velocity | ≦2 cm/min |

*Column equilibration is continued with additional buffer if the pH or conductivity targets are not met The final chromatographic step in the purification process is an anion exchange chromatography step, in this example Toyopearl QAE 550C, that adsorbs anionic contaminants from the rhIL-11 product stream: the rhIL-11 is recovered in the Toyopearl QAE unbound fraction.

Column operations are carried out at room temperature. The Toyopearl QAE 550C column is equilibrated first with 1M Glycine, pH 9.5 and then with 40 mM Glycine, pH 9.5. The diluted CM Sepharose peak is pumped through the column and chased with additional 40 mM Glycine, pH 9.5 to wash the remaining rhIL-11 product in the load out of the column. The unbound load effluent and the wash are collected into a storage vessel. This pool is then neutralized by the addition of 5% (v/v) 870 mM NaH$_2$PO$_4$, pH 5.0. Column operating parameters are detailed in Table 11.

Recovery of rhIL-11 for this step averages approximately 95%. Thioredoxin/rhIL-11 fusion protein that is not removed before this step is consistently removed to a level below detection by SDS-PAGE. The eluate pool contains highly purified rhIL-11, with minor amounts (<5%) of shorter length rhIL-11 molecules.

TABLE 11

Operating Parameters for the Toyopearl QAE Step

| Procedure | Parameter | Recommended Target |
|---|---|---|
| Column Packing: Toyopearl QAE 550C | Bed height | 20–22 cm |
| Equilibration 1 | volume | ≧1.3 column volumes |
|  | linear velocity | ≦2.6 cm/min |
| Equilibration 2 | pH | 9.3–9.7 |
|  | conductivity | ≦1.1 mS/cm |
|  | volume* | ≧3 column volumes |
|  | linear velocity | ≦2.6 cm/min |
| Load | volume | ≦7.5 column volumes |
|  | temperature | ≧15° C. |
|  | linear velocity | ≦2.6 cm/min |
| Wash | linear velocity | ≦2.6 cm/min |
| Neutralization | volume of neutralization solution | 5% (v/v) of flow-through pool |

*Column equilibration is continued with additional 40 mM Glycine, pH 9.5, if the pH or conductivity targets are not met.

While the present invention has been described in terms of specific methods and compositions, it is understood that variations and modifications will occur to those skilled in the art upon consideration of the present invention. The effective reagent concentrations, pH, and temperatures are process and protein specific and can he readily adjusted according to the nature of the anionic contaminants and chemical characteristics and stability of the protein of interest as is readily apparent to one skilled in the art.

Numerous modifications and variations in the invention as described in the above illustrative examples are expected to occur to those skilled in the art and, consequently, only such limitations as appear in the appended claims should be placed thereon. Accordingly, it is intended in the appended claims to cover all such equivalent variations which come within the scope of the invention as claimed.

What is claimed:

1. A method for separating a thioredoxin-like fusion protein from *E. coli*, including negatively charged non-proteinaceous material, into a solution comprising the steps of:

releasing said protein from said *E. coli* to said solution by adding chelator to said solution, and precipitating said negatively charged non-proteinaceous material from said solution by adding a divalent cation/alcohol solution to said solution to form a first soluble fraction and a first insoluble fraction, said first soluble fraction containing said protein.

2. The method of claim 1 further comprising the step of: isolating said protein from said first soluble fraction.

3. The method of claim 1 further comprising the step of: raising the temperature of said solution.

4. The method of claim 3, wherein said temperature is raised about 20 to 40 degrees Celsius.

5. The method of claim 4, wherein said temperature is raised from about 3° C. to about 37° C.

6. The method of claim 1, wherein said chelator is a member selected from the group consisting of EDTA, EGTA CDTA DPTA, and citric acid.

7. The method of claim 6, wherein said chelator is EDTA.

8. The method of claim 6, wherein the final concentration of said EDTA is 0.1 to 100 mM.

9. The method of claim 6, wherein the final concentration of said EDTA is 15 mM.

10. The method of claim 1, wherein said divalent cation is a member selected from the group consisting of magnesium manganese, and calcium.

11. The method of claim 1, wherein said divalent cation/ alcohol solution is a magnesium/manganese/calcium/ alcohol solution.

12. The method of claim 1, wherein said divalent cation/ alcohol solution is a magnesium/calcium/alcohol solution.

13. The method of claim 1, wherein said divalent cation/ alcohol solution is a magnesium/manganese/calcium/ alcohol solution.

14. The method of claim 1, wherein said divalent cation/ alcohol solution is magnesium/alcohol.

15. The method of claim 1, wherein said alcohol is a member selected from the group consisting of methanol, ethanol, propanol, isopropanol, iso-butanol, and tertiary-butanol.

16. The method of claim 1, wherein said alcohol is ethanol.

17. The method of claim 1, wherein the final concentration of said alcohol is from 5 to 30%.

18. The method of claim 16, wherein the final concentration of said alcohol is 14%.

19. The method of claim 1, wherein said divalent cation final concentration ranges from 1 to 1000 mM.

20. The method of claim 19, wherein said divalent cation final concentration ranges from 50 to 200 mM.

21. The method of claim 19, wherein said magnesium final concentration is 200 mM.

22. The method of claim 19, wherein said magnesium final concentration is 125 mM, and calcium final concentration is 75 mM.

23. The method of claim 19, wherein said magnesium final concentration is 125 mM, and manganese final concentration is 75 mM.

24. The method of claim 19, wherein said magnesium final concentration is 125 mM, manganese final concentration is 38 mM and said calcium final concentration is 38 mM.

25. The method of claim 1, further comprising the step of:
precipitating said protein from said first soluble fraction by adding zinc to said first soluble fraction to form a second insoluble fraction and a second soluble fraction.

26. The method of claim 19, further comprising the step of isolating said protein from said second insoluble fraction.

27. The method of claim 19, further comprising the step of adding chelator to solubilize said protein from said second insoluble fraction.

28. The method of claim 19, wherein said zinc is a member selected from the group consisting of zinc chloride, zinc sulphate, and zinc acetate.

29. The method of claim 19, wherein said zinc final concentration is 1 to 500 mM.

30. The method of claim 19, wherein said zinc final concentration is 50 mM zinc chloride.

31. The method of claim 1, wherein said protein is recombinantly produced in a transformed host cell.

32. A method for purification of a protein in solution, wherein said solution contains negatively charged non-proteinaceous material, comprising the steps of:
precipitating said negatively charged non-proteinaceous material by adding a divalent cation/alcohol solution to said solution to form a first soluble fraction, containing said protein, and a first insoluble fraction, containing said negatively charged non-proteinaceous material.

33. The method of claim 32, further comprising the step of:
isolating said protein from said first soluble fraction.

34. The method of claim 32, wherein said divalent cation is a member selected from the group consisting of magnesium, manganese, and calcium.

35. The method of claim 32, wherein said alcohol is a member selected from the group consisting of methanol, ethanol, propanol, isopropanol, iso-butanol, and tertiary-butanol.

36. The method of claim 32, wherein said alcohol is ethanol.

37. The method of claim 32, wherein the final concentration of said alcohol is from 5 to 30%.

38. The method of claim 32, wherein the final concentration of said alcohol is 14%.

39. The method of claim 32, wherein the final concentration of said divalent cation is from 1 to 1000 mM.

40. The method of claim 32 wherein said magnesium final concentration is 200 mM.

41. The method of claim 32, wherein said magnesium final concentration is 125 mM, and said calcium final concentration is 75 mM.

42. A method for purifying a protein of interest, wherein a protein prior to cleavage is negatively charged and comprises a fusion partner and said protein of interest and after cleavage is a positively charged protein of interest, comprising the steps of:
binding said negatively charged protein to a first anion exchange resin, eluting said negatively charged protein with a first eluant to form a first eluate, applying said first eulate to a first cation exchange resin, collecting said negatively charged protein, in an unbound fraction, from said first cation exchange resin, cleaving said negatively charged protein, to form a positively charged protein, binding said positively charged protein to a second cation exchange resin, eluting said positively charged protein with a second eluant to form a second eluate, applying said second eluate to a second anion exchange resin, and collecting said positively charged protein in an unbound fraction, from said second anion exchange resin.

43. The method of claim 42, wherein said protein is a thioredoxin fusion protein.

44. The method of claim 43, wherein said thioredoxin fusion protein comprises thioredoxin and IL-11.

45. The method of claim 42, wherein said first and said second anion exchange resins are anion exchange resins having positively charged members selected from the group consisting of diethyleaminoethane (DEAE), polyethyleneimine (PEI), and quaternary aminoethane (QAE).

46. The method of claim 42, wherein said first and second cation exchange resins are cation exchange resins having negatively charged members selected from the group consisting of sulfonyl, sulfylpropyl (SP), carboxyl, and carboxy methyl.

47. The method of claim 44, wherein said first eluant is a member selected from the group consisting of:
(a) 20 to 100 mM Tris, at pH 7.5 to 8.5, 100–500 mM NaCl and
(b) 50 to 200 mM histidine buffer, at pH 5.5 to 6.6, 0 to 150 mM NaCl.

48. The method of claim 44, wherein said second eluant is 50 to 300 mM glycine buffer, pH 9.0 to 10.0, and 100 to 500 mM NaCl.

49. A method for purifying a protein, comprising the steps of:
binding a fusion protein to a first resin, eluting said fusion protein with a first eluant to form a first eluate, applying said first eluate to a second resin, collecting said fusion protein in an unbound fraction from said second resin, cleaving said fusion protein to form cleaved protein, binding said cleaved protein to a third resin, eluting said protein with a third eluant to form a third eluate, applying said third eluate to a fourth resin, and collecting said protein in an unbound fraction from said fourth resin.

50. The method of claim 49, wherein said fusion protein is negatively charged prior to cleavage.

51. The method of claim 49, wherein said fusion protein is a thioredoxin fusion protein.

52. The method of claim 50, wherein said first and fourth resin is an anion exchange resin and wherein said second and third resin is a cation exchange resin.

53. The method of claim 44, wherein said fusion protein is positively charged prior to cleavage.

54. The method of claim 53, wherein said first and fourth resin is a cation exchange resin and wherein said second and third resin is an anion exchange resin.

55. A method for purifying a protein, comprising the steps of:

applying a fusion protein to a first resin, collecting said fusion protein in an unbound fraction from said first resin, binding said fusion protein to a second resin, eluting said fusion protein with a first eluant to form a first eluate, cleaving said fusion protein to form cleaved protein, binding said cleaved protein to a third resin, eluting said protein with a second eluant to form a second eluate, applying said second eluate to a fourth resin, and collecting said protein in an unbound fraction from said fourth resin.

56. The method of claim 55, wherein said fusion protein is a thioredoxin fusion protein.

57. The method of claim 56, wherein said thioredoxin fusion protein is thioredoxin/IL-11 fusion protein.

58. The method of claim 55, wherein said fusion protein is negatively charged prior to cleavage.

59. The method of claim 58, wherein said first and third resin is a cation exchange resin and wherein said second and fourth resin is an anion exchange resin.

60. The method of claim 55, wherein said fusion protein is positively charged prior to cleavage.

61. The method of claim 60, wherein said first and third resin is an anion exchange resin and where said second and fourth resin is a cation exchange resin.

62. A method for purifying a protein, comprising the steps of:

applying a fusion protein to a first resin, collecting said fusion protein in an unbound fraction from said first resin, binding said fusion protein to a second resin, eluting said fusion protein from said second resin with a first eluant to form a first eluate, cleaving said fusion protein to form cleaved protein, applying said cleaved protein to a third resin, collecting said protein in an unbound fraction from said third resin, binding said protein to a fourth resin, and eluting said protein from said fourth resin.

63. The method of claim 62, wherein said fusion protein is a thioredoxin fusion protein.

64. The method of claim 62, wherein said fusion protein is negatively charged prior to cleavage.

65. The method of claim 63, wherein said thioredoxin fusion protein is thioredoxin/IL-11 fusion protein.

66. The method of claim 64, wherein said first and fourth resin is a cation exchange resin and wherein said second and third resin is an anion exchange resin.

67. The method of claim 63, wherein said fusion protein is positively charged prior to cleavage.

68. The method of claim 67, wherein said first and fourth resin is an anion exchange resin and wherein said second and third resin is a cation exchange resin.

69. A method for purifying a protein, comprising the steps of:

binding a fusion protein to a first resin, eluting said fusion protein from said first resin with a first eluant to form a first eluate, applying said first eluate to a second resin, collecting said fusion protein in an unbound fraction from said second resin, cleaving said fusion protein to form cleaved protein, applying said cleaved protein to a third resin, collecting said protein in an unbound fraction from said third resin, binding said protein to a fourth resin, and eluting, said protein from said fourth resin.

70. The method of claim 69, wherein said fusion protein is a thioredoxin fusion protein.

71. The method of claim 69, wherein said fusion protein is negatively charged prior to cleavage.

72. The method of claim 70, wherein said thioredoxin fusion protein is thioredoxin/IL-11 fusion protein.

73. The method of claim 71, wherein said first and third resin is an anion exchange resin and wherein said second and fourth resin is a cation exchange resin.

74. The method of claim 69, wherein said fusion protein is positively charged prior to cleavage.

75. The method of claim 74, wherein said first and third resin is a cation exchange resin and wherein said second and fourth resin is an anion exchange resin.

76. A method for purifying IL-11, comprising the steps of:

binding thioredoxin-IL-11 to a first anion exchange resin, eluting with a first eluant to form a first eluate, applying said first eluate to a first cation exchange resin, collecting said thioredoxin-IL-11, in an unbound fraction, from said first cation exchange resin, cleaving said thioredoxin-IL-11 fusion protein to form positively charged IL-11, binding said positively charged IL-11 to a second cation exchange resin, eluting said IL-11 with a second eluant to form a second eluate, applying said second eluate to a second anion exchange resin, collecting said IL-11, in an unbound fraction, from said second anion exchange resin.

77. The method of claim 76, wherein said first and second anion exchange resins are anion exchange resins having positively charged members selected from the group consisting of diethyleaminoethane (DEAE), polyethyleneimine (PEI), and quaternary aminoethane (QAE).

78. The method of claim 77, wherein said anion exchange resin is quaternary aminoethane.

79. The method of claim 76, wherein said first and second cation exchange resins are cation exchange resins having negatively charged members selected from the group consisting of sulfonyl, sulfylpropyl (SP), carboxyl, and carboxy methyl.

80. The method of claim 79, wherein said first cation exchange resin is sulfonyl.

81. The of claim 79, wherein said second cation exchange resin is carboxy methyl.

82. The method of claim 76, wherein said first eluant is a member of the group consisting of:
(a) 20 to 100 mM Tris, at pH 7.5 to 8.5, 100–500 mM NaCl and
(b) 50 to 200 mM histidine buffer, at pH 5.5 to 6.6, 0 to 150 mM NaCl.

83. The method of claim 76, wherein said second eluant is 50 to 300 mM glycine buffer, pH 9.0 to 10.0, and 100 to 500 mM NaCl.

84. A method for purifying IL-11, comprising the steps of:
binding thioredoxin-IL-11 to quaternary amino ethane, eluting with 75 mM NaCl, 75 mM histidine, pH 6.2,
applying said first eluate to sulfonyl,
collecting said thioredoxin-L-11 in an unbound fraction from said sulfonyl,
cleaving said thioredoxin-IL-11 fusion protein to form positively charged IL-11,
binding said positively charged IL-11 to carboxymethyl,
eluting said IL-11 with 0.15M glycine, 0.15M NaCl, pH 9.5,
applying said second eluate to quaternary amino ethane, and
collecting said IL-11 in an unbound fraction from said quaternary amino ethane.

85. A method for purifying a protein of interest,
wherein said protein prior to cleavage is a fusion protein comprising a fusion partner, said fusion protein being negatively charged and,
wherein said protein after cleavage from said fusion protein is positively charged, comprising the steps of:
a) selecting a step selected from the group consisting of:
  i) binding said negatively charged fusion protein to an anion exchange resin and eluting said negatively charged fusion protein, and
  ii) applying said negatively charged fusion protein to a cation exchange resin and collecting said negatively charged fusion protein in an unbound fraction,
b) cleaving said negatively charged fusion protein to form said positively charged protein of interest, and
c) selecting a step selected from the group consisting of:
  i) binding said positively charged protein to a cation exchange resin and eluting said positively charged protein, and
  ii) applying said positively charged protein to an anion exchange resin and collecting said positively charged protein in an unbound fraction.

86. A method for purifying a protein of interest,
wherein said protein prior to cleavage is a fusion protein comprising a fusion partner, said fusion protein being positively charged and,
wherein said protein after cleavage from said fusion protein is negatively charged, comprising the steps of:
a) selecting a step selected from the group consisting of:
  i) binding said positively charged fusion protein to an cation exchange resin and eluting said positively charged fusion protein, and
  ii) applying said positively charged fusion protein to an anion exchange resin and collecting said positively charged fusion protein in an unbound fraction,
b) cleaving said positively charged fusion protein to form said negatively charged protein of interest, and
c) selecting a step selected from the group consisting of:
  i) binding said negatively charged protein to an anion exchange resin and eluting said negatively charged protein, and
  ii) applying said negatively charged protein to a cation exchange resin and collecting said negatively charged protein in an unbound fraction.

87. A method for separating a thioredoxin IL-11 fusion protein from E. coli, including negatively charged non-proteinaceous material, into a solution comprising the steps of:
releasing said protein from said E. coli to said solution by adding chelator to said solution, and
precipitating said negatively charged non-proteinaceous material from said solution by adding a divalent cation/alcohol solution to said solution to form a first soluble fraction and a first insoluble fraction, said first soluble fraction containing said protein.

88. The method of claim 87, wherein said chelator is a member selected from the group consisting of EDTA, EGTA, CDTA, DPTA, and citric acid.

89. The method of claim 87, wherein said divalent cation is a member selected from the group consisting of magnesium, manganese, and calcium.

90. The method of claim 87, wherein said divalent cation/alcohol solution is magnesium/ethanol.

91. The method of claim 87, wherein said divalent calcium/alcohol solution is magnesium/calcium/ethanol.

92. The method of claim 88, wherein the final concentration of said EDTA ranges from 0.1 to 100 mM.

93. The method of claim 92, wherein the final concentration of said EDTA is 15 mM.

94. The method of claim 90, wherein the final concentration of said magnesium ranges from 1 to 1000 mM and the final concentration of said ethanol ranges from 5 to 30%.

95. The method of claim 94, wherein said magnesium final concentration is 200 mM, and said ethanol final concentration is 14%.

96. The method of claim 91, wherein the final concentration of said magnesium ranges from 1 to 1000 mM, the final concentration of said calcium ranges from 1 to 1000 mM, and the final concentration of said ethanol ranges from 5 to 30%.

97. The method of claim 96, wherein said magnesium final concentration is 125 mM, said calcium final concentration is 75 mM, and said ethanol final concentration is 14%.

98. A method for separating a thioredoxin IL-11 fusion protein from E. coli, including negatively charged non-proteinaceous material, into a first solution comprising the steps of:
releasing said protein from said E. coli to said first solution by adding EDTA to said solution, precipitating said negatively charged non-proteinaceous material from said first solution by adding a second solution comprising MgCl$_2$, CaCl$_2$ and ethanol to said first solution to form a first soluble fraction and a first insoluble fraction, said first soluble fraction containing said protein.

99. The method of claim 98, wherein the final concentration of said EDTA ranges from 0.1 to 00 mM.

100. The method of claim 99, wherein the final concentration of said EDTA is 15 mM.

101. The method of claim 98, wherein the final concentration of said MgCl$_2$ and CaCl$_2$ ranges from 1 to 1000 mM and the final concentration of said ethanol ranges from 5 to 30%.

102. The method of claim 101, wherein said MgCl$_2$ final concentration is 125 mM, said CaCl$_2$ final concentration is 75 mM and said ethanol final concentration is 14%.

103. The method of claim 98, further comprising the step of isolating said protein from said first soluble fraction.

* * * * *

UNITED STATES PATENT AND TRADEMARK OFFICE
CERTIFICATE OF CORRECTION

PATENT NO. : 5,760,189

DATED : June 2, 1998

INVENTOR(S) : Steven M. Vicik et al

It is certified that error appears in the above-identified patent and that said Letters Patent is hereby corrected as shown below:

On the Title Page : [57], Abstract, line 3, after "purification", please insert --of --

At column 1, line 21, replace "head" with -- bead--.
At column 1, line 48, replace "Coli" with -- coli- -.
At column 1, line 58, replace "ionic" with -- Ionic --.
At column 1, line 62, replace "X-1100" with -- X100 --.
At column 2, line 10, replace "lysozyine" with -- lysozyme --.
At column 2, line 11, replace "its" with -- the --.
At column 2, line 22, delete -- of the protein --.
At column 4, line 50, replace "C." with -- C --.
At column 7, line 14, replace "contaminants)" with -- contaminants --.
At column 8, line 58, replace "he" with -- be --.
At column 16, line 9, replace "NuCleotides" with -- nucleotides --.
At column 20 line 28, replace "addling" with -- adding --.
At column 20, line 34, replace "ad just" with -- adjust --.
At column 20, line 40, replace "Branford" with -- Bradford --.

UNITED STATES PATENT AND TRADEMARK OFFICE
CERTIFICATE OF CORRECTION

PATENT NO. : 5,760,189

DATED : June 2, 1998

INVENTOR(S) : Steven M. Vicik et al

It is certified that error appears in the above-identified patent and that said Letters Patent is hereby corrected as shown below:

At column 21, line 36, replace "the" with -- of the --.
At column 24, line 47, replace "6.2.Next" with -- 6.2. Next, --.
At column 30, line 27, replace "eulate" with -- eluate --.
At column 35, line 8, replace "00" with -- 100 --.

Signed and Sealed this

Fifteenth Day of May, 2001

Attest:

NICHOLAS P. GODICI

*Attesting Officer*    *Acting Director of the United States Patent and Trademark Office*